US009968973B2

(12) United States Patent
Kosugi

(10) Patent No.: US 9,968,973 B2
(45) Date of Patent: May 15, 2018

(54) ENDOSCOPE REPROCESSOR

(71) Applicant: OLYMPUS CORPORATION, Tokyo (JP)

(72) Inventor: Aiko Kosugi, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/373,576

(22) Filed: Dec. 9, 2016

(65) Prior Publication Data
US 2017/0087604 A1 Mar. 30, 2017

Related U.S. Application Data

(63) Continuation of application No. PCT/JP2016/059010, filed on Mar. 22, 2016.

(30) Foreign Application Priority Data

Sep. 2, 2015 (JP) ................. 2015-173178

(51) Int. Cl.
*B08B 9/032* (2006.01)
*A61B 1/00* (2006.01)
(Continued)

(52) U.S. Cl.
CPC ........ *B08B 9/0325* (2013.01); *A61B 1/00059* (2013.01); *A61B 1/12* (2013.01);
(Continued)

(58) Field of Classification Search
CPC ... B08B 9/0323; A61B 1/00059; A61B 1/123; A61B 1/125
(Continued)

(56) References Cited

U.S. PATENT DOCUMENTS

2007/0089487 A1* 4/2007 Jackson ............. A61B 1/00057
73/37
2007/0100204 A1* 5/2007 Feld ................... A61B 1/00057
600/117
(Continued)

FOREIGN PATENT DOCUMENTS

JP H04-017835 A 1/1992
JP H06-343607 A 12/1994
(Continued)

OTHER PUBLICATIONS

JPH0417835—Machine Translation, Jan. 1992.*
JP 2002282200—Machine Translation, Oct. 2002.*

*Primary Examiner* — Marc Lorenzi
(74) *Attorney, Agent, or Firm* — Scully, Scott, Murphy & Presser, P.C.

(57) ABSTRACT

An endoscope reprocessor includes: an endoscope information reading section configured to read endoscope information from each of endoscopes; a treatment tank in which the endoscopes are disposed; a number detection section configured to detect a number of the endoscopes disposed in the treatment tank; a determination section configured to determine whether a first number that is the number of endoscopes read by the endoscope information reading section is equal to a second number that is the number of the endoscopes detected by the number detection section; a notification section configured to execute error notification; and a control section connected with the determination section and the notification section, and configured to drive the notification section when the determination section determines that the first number is different from the second number.

1 Claim, 13 Drawing Sheets

(51) Int. Cl.
  *A61B 1/12*   (2006.01)
  *B08B 3/08*   (2006.01)
  *B08B 9/023*   (2006.01)
  *G08B 21/18*   (2006.01)
  *G02B 23/24*   (2006.01)

(52) U.S. Cl.
  CPC ............... *A61B 1/123* (2013.01); *B08B 3/08* (2013.01); *B08B 9/023* (2013.01); *B08B 9/0323* (2013.01); *G02B 23/24* (2013.01); *G08B 21/187* (2013.01)

(58) Field of Classification Search
  USPC .................................................. 600/117, 133
  See application file for complete search history.

(56) References Cited

U.S. PATENT DOCUMENTS

| | | | |
|---|---|---|---|
| 2010/0071736 A1* | 3/2010 | Watanabe | A61B 1/00006 134/56 R |
| 2014/0166059 A1* | 6/2014 | Kosugi | B08B 9/02 134/113 |
| 2016/0081540 A1 | 3/2016 | Suzuki | |

FOREIGN PATENT DOCUMENTS

| | | |
|---|---|---|
| JP | 2002-282200 A | 10/2002 |
| JP | 2010-035689 A | 2/2010 |
| JP | 5802859 B1 | 11/2015 |
| WO | WO 2015/111251 A1 | 7/2015 |

* cited by examiner

ENDOSCOPE REPROCESSOR

CROSS REFERENCE TO RELATED APPLICATION

This application is a continuation application of PCT/JP2016/059010 filed on Mar. 22, 2016 and claims benefit of Japanese Application No. 2015-173178 filed in Japan on Sep. 2, 2015, the entire contents of which are incorporated herein by this reference.

BACKGROUND OF THE INVENTION

1. Field of the Invention

The present invention relates to an endoscope reprocessor including an endoscope information reading section that reads endoscope information.

2. Description of the Related Art

An endoscope used in a medical field is subjected to reprocessing using a medicinal solution, such as cleaning treatment and disinfecting treatment after use. In addition, an endoscope cleaning apparatus configured to automatically perform the reprocessing of the endoscope is well-known.

For example, as disclosed in Japanese Patent Application Laid-Open Publication No. 2010-35689, an endoscope cleaning apparatus is well-known that includes an endoscope information reading section configured to read endoscope information from an RFID tag or the like provided in the endoscope, and associates the endoscope information with history information of performing of reprocessing.

SUMMARY OF THE INVENTION

An endoscope reprocessor according to an aspect of the present invention includes: an endoscope information reading section configured to read endoscope information from each of endoscopes; a treatment tank in which the endoscopes are disposed; a number detection section configured to detect a number of the endoscopes disposed in the treatment tank; a determination section configured to determine whether a first number that is the number of the endoscopes read by the endoscope information reading section is equal to a second number that is the number of the endoscopes detected by the number detection section; a notification section configured to execute error notification; and a control section connected with the determination section and the notification section, and configured to drive the notification section when the determination section determines that the first number is different from the second number.

DETAILED DESCRIPTION OF THE PREFERRED EMBODIMENT(S)

Figure 1:
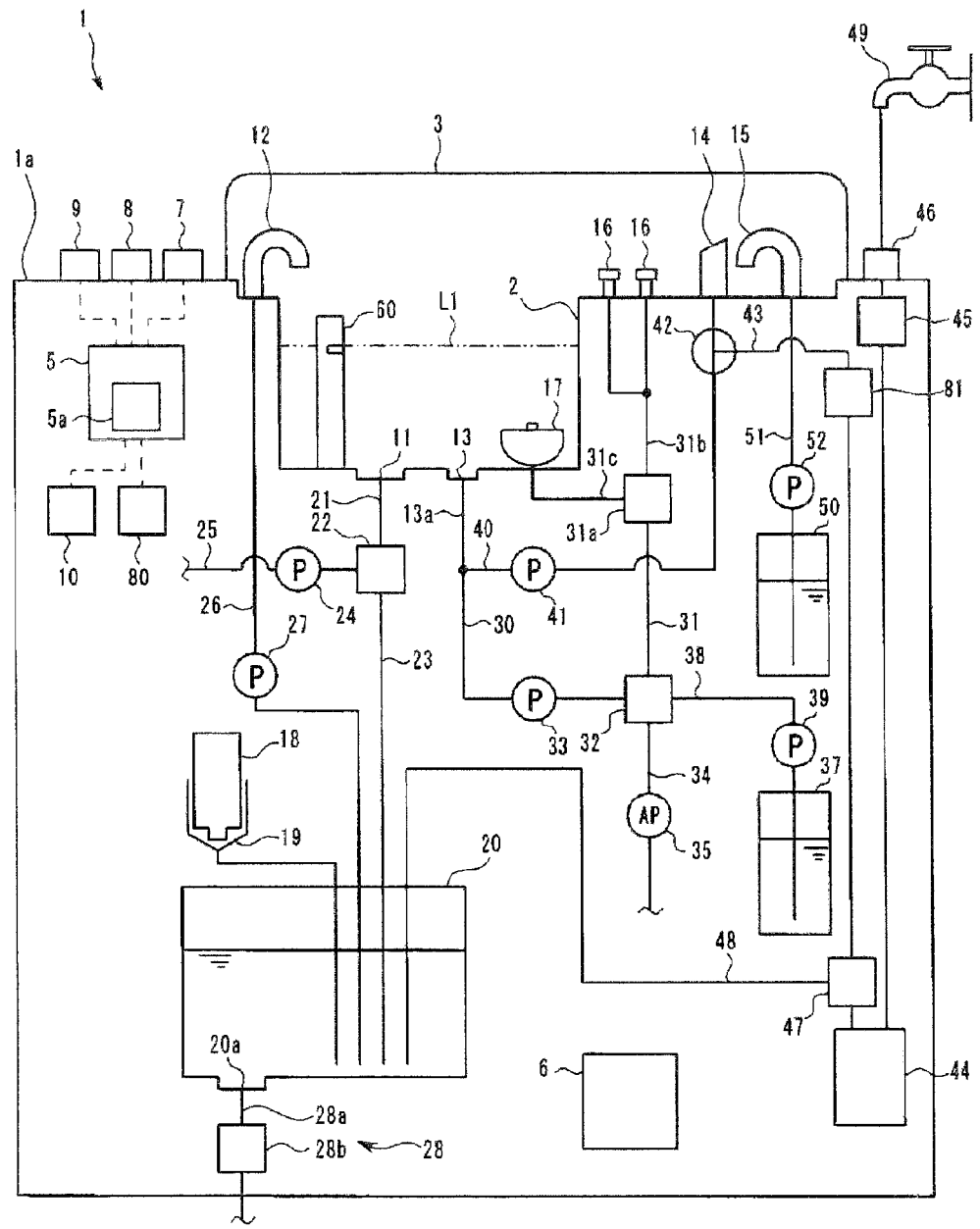
FIG. 1 is a diagram illustrating a configuration of an endoscope reprocessor according to a first embodiment.

Some preferred embodiments of the present invention are described below with reference to drawings. Note that, in the drawings used in the following description, to illustrate respective components to a recognizable extent on the drawings, a scale is varied for each component. The present invention is not limited to the number of components, the shapes of the respective components, the size ratio of the components, and relative positional relationship of the respective components that are illustrated in the drawings.

First Embodiment

An example of the embodiments of the present invention is described below. An endoscope reprocessor 1 illustrated in FIG. 1 is an apparatus configured to perform reprocessing on an endoscope. The reprocessing used herein is not particularly limited, and may include rinsing treatment with water, cleaning treatment for removing contaminants such as organic matter, disinfecting treatment for neutralizing predetermined microorganisms, sterilizing treatment for eliminating or killing all of microorganisms, or any combination of the treatments.

Note that, in the following description, an upper part indicates a position far away from the ground relative to a comparison object, and a lower part indicates a position closer to the ground relative to the comparison object. In addition, low and high in the following description indicates height relationship along the gravity direction.

The endoscope reprocessor 1 includes a control section 5, a power supply section 6, an operation section 7, a notification section 8, a treatment tank 2, an endoscope information reading section 9, a number detection section 80, and a determination section 10.

The control section 5 may include a processor unit (CPU), a memory device (RAM), an auxiliary memory device, an input-output device, a power control device, and the like, and is configured to control motion of the respective parts configuring the endoscope reprocessor 1, based on predetermined programs. The motion of the respective components included in the endoscope reprocessor 1 in the following description is controlled by the control section 5 even if particular description is not given.

The power supply section 6 supplies power to the respective parts of the endoscope reprocessor 1. The power supply section 6 distributes power that is externally supplied from a commercial power supply or the like, to the respective parts. Note that the power supply section 6 may include a power generator and a battery.

The operation section 7 and the notification section 8 configure a user interface that receives and transfers information from/to a user. The operation section 7 includes an operation member that receives motion instruction from the user, such as a push switch and a touch sensor. The motion instruction from the user is converted into an electrical signal by the operation section 7, and the electrical signal is provided to the control section 5. The operation instruction from the user may be, for example, starting instruction of the reprocessing. Note that the operation section 7 may be provided in an electronic apparatus that is separated from a main body section 1*a* of the endoscope reprocessor 1 and performs wired communication or wireless communication with the control section 5.

Also, the notification section 8 includes, for example, a display device that displays images and characters, a light emitting device that emits light, a speaker that emits sound, a vibrator that generates vibration, or any combination of these devices. The notification section 8 provides information from the control section 5 to the user. Note that the notification section 8 may be provided in the electronic apparatus that is separated from the main body section 1*a* of the endoscope reprocessor 1 and performs wired communication or wireless communication with the control section 5.

When an abnormality (an error) occurs in the motion of the endoscope reprocessor 1, the control section 5 drives the notification section 8, thereby providing error notification through, for example, sound emission. Also, the notification section 8 may include a configuration to display character information that indicates error contents in the error notification.

The treatment tank 2 has a concave shape including an opening portion and can reserve liquid inside the treatment tank 2. A plurality of endoscopes not illustrated may be disposed inside the treatment tank 2. In the present embodiment, two endoscopes may be disposed, as an example, in the treatment tank 2. A cover 3 that opens and closes the opening portion of the treatment tank 2 is provided at an upper part of the treatment tank 2. To perform the reprocessing on the endoscopes in the treatment tank 2, the opening portion of the treatment tank 2 is closed by the cover 3.

The treatment tank 2 is provided with a medicinal solution nozzle 12, a liquid discharge port 11, a circulation port 13, a circulation nozzle 14, a disinfectant liquid nozzle 15, an endoscope connection portion 16, an accessory case 17, and a first water level sensor 60.

The medicinal solution nozzle 12 is an opening portion that communicates with a medicinal solution tank 20 through a medicinal solution conduit 26. The medicinal solution tank 20 reserves medicinal solution. The medicinal solution conduit 26 is provided with a medicinal solution pump 27. Operating the medicinal solution pump 27 transfers the medicinal solution in the medicinal solution tank 20 to the treatment tank 2 through the medicinal solution conduit 26 and the medicinal solution nozzle 12. The medicinal solution pump 27 is connected with the control section 5, and the motion of the medicinal solution pump 27 is controlled by the control section 5.

A kind of the medicinal solution reserved in the medicinal solution tank 20 is not particularly limited; however, examples of the medicinal solution in the present embodiment may include a disinfectant liquid used in disinfecting treatment and a sterile liquid used in sterilization treatment. Examples of the disinfectant liquid and the sterile liquid may include peracetic acid. The medicinal solution of present invention, however, is not limited to the above-described examples, and a cleaning liquid used for cleaning treatment, highly volatile solution used for drying, and the like may be appropriately selected as the medicinal solution according to a purpose.

In addition, in the present embodiment, the medicinal solution as an example is obtained by diluting a stock solution of the medicinal solution supplied from a medicinal solution bottle 18 with water at predetermined ratio. The medicinal solution tank 20 according to the present embodiment communicates with a bottle connection portion 19 and a diluting conduit 48. The bottle connection portion 19 introduces the stock solution of the medicinal solution supplied from the medicinal solution bottle 18, to the medicinal solution tank 20. The diluting conduit 48 introduces water for diluting, to the medicinal solution tank 20. The medicinal solution bottle 18 is connected with the bottle connection portion 19, which causes the stock solution of the medicinal solution to be led into the medicinal solution tank 20. The configuration to introduce water from the diluting conduit 48 to the medicinal solution tank 20 is described later.

Note that the endoscope reprocessor 1 may not include the configuration in which the medicinal solution is diluted with water or the like. Also, in a case where a plurality of kinds of stock solution are mixed and used as the medicinal solution, the bottle connection portion 19 is connectable with a plurality of medicinal solution bottles 18.

Further, as an example in the present embodiment, when the medicinal solution has concentration that is within a predetermined medicinal range, the medicinal solution is reusable. The medicinal solution tank 20 also functions as a medicinal solution recovery section that recovers and reserves again the medicinal solution that has been transferred from the medicinal solution tank 20 to the treatment tank 2.

Also, a liquid discharge portion 28 is disposed in the medicinal solution tank 20. The liquid discharge portion 28 discharges the liquid such as the medicinal solution and water from the medicinal solution tank 20. The liquid discharge portion 28 may have a configuration to discharge the liquid from the medicinal solution tank 20 by the gravity, or a configuration to forcibly discharge the liquid from the medicinal solution tank 20 with use of a pump.

As an example in the present embodiment, the liquid discharge portion 28 includes a drain conduit 28*a* and a drain valve 28*b*. The drain conduit 28*a* communicates with a liquid discharge port 20*a* that is provided on or in the vicinity of a bottom surface of the medicinal solution tank 20. The drain valve 28*b* opens and closes the drain conduit 28*a*. The drain valve 28*b* may be an electromagnetic stop valve that is opened or closed by the control section 5, or may be a cock that is opened or closed by manual operation of the user.

Note that a path to discharge the liquid from the medicinal solution tank 20 is not limited to the drain conduit. For example, starting the operation of the medicinal solution pump 27 may cause the liquid to be discharged from the medicinal solution tank 20 to the treatment tank 2 through the medicinal solution conduit 26 and the medicinal solution nozzle 12. In this case, the endoscope reprocessor 1 may have a configuration not including the liquid discharge port 20a, the drain conduit 28a, and the drain valve 28b that are illustrated in FIG. 1.

The liquid discharge port 11 is an opening portion that is provided at the lowest part in the treatment tank 2. The liquid discharge port 11 is connected with a discharge conduit 21. The discharge conduit 21 makes the liquid discharge port 11 communicate with a selector valve 22. A recovery conduit 23 and a discarding conduit 25 are connected with the selector valve 22. The selector valve 22 can be switched among a state of closing the discharge conduit 21, a state of making the discharge conduit 21 communicate with the recovery conduit 23, and a state of making the discharge conduit 21 communicate with the discarding conduit 25. The selector valve 22 is connected with the control section 5, and the motion of the selector valve 22 is controlled by the control section 5.

The recovery conduit 23 makes the medicinal solution tank 20 communicate with the selector valve 22. Further, a discharge pump 24 is provided in the discarding conduit 25. The discharge pump 24 is connected with the control section 5, and the motion of the discharge pump 24 is controlled by the control section 5. The discarding conduit 25 is connected with liquid discharging equipment that receives the liquid discharged from the endoscope reprocessor 1.

When the selector valve 22 is closed, the liquid is reserved in the treatment tank 2. Also, when the selector valve 22 is put into the state of making the discharge conduit 21 communicate with the recovery conduit 23 while the medicinal solution is reserved in the treatment tank 2, the medicinal solution is transferred from the treatment tank 2 to the medicinal solution tank 20. Further, when the selector valve 22 is put into the state of making the discharge conduit 21 communicate with the discarding conduit 25 and the operation of the discharge pump 24 is then started, the liquid in the treatment tank 2 is delivered to the liquid discharge equipment through the discarding conduit 25.

The circulation port 13 is an opening portion that is provided in the vicinity of the bottom surface of the treatment tank 2. The circulation port 13 communicates with the circulation conduit 13a. The circulation conduit 13a is branched into two conduits of an endoscope circulation conduit 30 and a treatment tank circulation conduit 40.

The endoscope circulation conduit 30 makes the circulation conduit 13a communicate with a channel block 32 described later. The endoscope circulation conduit 30 is provided with a circulation pump 33. The circulation pump 33 operates to transfer the fluid inside the endoscope circulation conduit 30 toward the channel block 32.

An air intake conduit 34, an alcohol conduit 38, and a delivery conduit 31 are connected with the channel block 32, in addition to the above-described endoscope circulation conduit 30. The channel block 32 connects the delivery conduit 31 with the endoscope circulation conduit 30, the air intake conduit 34, and the alcohol conduit 38. The channel block 32 is provided with a check valve that allows a fluid to flow only in a direction from each of the endoscope circulation conduit 30, the air intake conduit 34, and the alcohol conduit 38 toward the inside of the channel block 32. In other words, the fluid is prevented from flowing from the inside of the channel block 32 toward the endoscope circulation conduit 30, the air intake conduit 34, and the alcohol conduit 38.

One of ends of the air intake conduit 34 is open to the atmosphere, and the other end is connected with the channel block 32. Note that, although not illustrated, the one of the ends of the air intake conduit 34 is provided with a filter that filters passing gas. An air pump 35 is provided in the air intake conduit 34, and operates to transfer the gas inside the air intake conduit 34 toward the channel block 32.

The alcohol conduit 38 makes an alcohol tank 37 that reserves alcohol communicate with the channel block 32. Examples of the alcohol reserved in the alcohol tank 37 may include ethanol. An alcohol concentration may be appropriately selected. An alcohol pump 39 is provided in the alcohol conduit 38, and operates to transfer the alcohol in the alcohol tank 37 toward the channel block 32.

The circulation pump 33, the air pump 35, and the alcohol pump 39 are connected with the control section 5, and the motion of these pumps is controlled by the control section 5. When the operation of the circulation pump 33 is started while the liquid is reserved in the treatment tank 2, the liquid in the treatment tank 2 is supplied to the delivery conduit 31 through the circulation port 13, the circulation conduit 13a, and the endoscope circulation conduit 30. Also, when the operation of the air pump 35 is started, the air is supplied to the delivery conduit 31. Further, when the operation of the alcohol pump 39 is started, the alcohol in the alcohol tank 37 is supplied to the delivery conduit 31.

The delivery conduit 31 is branched into an endoscope connection conduit 31b and a case connection conduit 31c. The endoscope connection conduit 31b is connected with the endoscope connection portion 16. Also, the case connection conduit 31c is connected with the accessory case 17.

Further, the delivery conduit 31 is provided with a flow path selector portion 31a. The flow path selector portion 31a is a relief valve that constantly connects the delivery conduit 31 with the endoscope connection conduit 31b. When the pressure inside the endoscope connection conduit 31b exceeds a predetermined value, the flow path selector portion 31a releases the fluid that flows from the delivery conduit 31, to the case connection conduit 31c. In other words, the flow path selector portion 31a maintains the pressure inside the endoscope connection conduit 31b constant.

The endoscope connection portion 16 may be connected, through an unillustrated cleaning tube, with a pipe sleeve provided in the endoscope, or may be directly connected with the endoscope. The endoscope connection portion 16 is provided by the number corresponding to the number of endoscopes arrangeable in the treatment tank 2. As mentioned above, as an example in the present embodiment, two endoscopes are arrangeable in the treatment tank 2. Therefore, at least two endoscope connection portions 16 are provided to be connectable with the respective pipe sleeves of the two endoscopes. The accessory case 17 is a basket-shaped member that houses unillustrated accessories of the endoscope.

The fluid delivered from the channel block 32 to the delivery conduit 31 is led into the conduit that communicates with the pipe sleeve of the endoscope, through the endoscope connection portion 16 and the cleaning tube. When the pressure of the fluid led into the conduit exceeds a value that causes the flow path selector portion 31a serving as the relief valve to operate, the fluid is also led into the accessory case 17 through the case connection conduit 31c, in addition to the conduit of the endoscope.

The treatment tank circulation conduit 40 makes the circulation conduit 13a communicate with the circulation nozzle 14. The circulation nozzle 14 is an opening portion provided inside the treatment tank 2. The treatment tank circulation conduit 40 is provided with a liquid flowing pump 41. The liquid flowing pump 41 is connected with the control section 5, and the motion of the liquid flowing pump 41 is controlled by the control section 5.

Also, a three-way valve 42 is provided in the treatment tank circulation conduit 40 between the liquid flowing pump 41 and the circulation nozzle 14. A water feed conduit 43 is connected with the three-way valve 42. The three-way valve 42 can be switched among a state of making the circulation nozzle 14 communicate with the treatment tank circulation conduit 40 and a state of making the circulation nozzle 14 communicate with the water feed conduit 43.

The water feed conduit 43 makes the three-way valve 42 communicate with a water supply source connection portion 46. The water feed conduit 43 is provided with a water lead-in valve 45 that opens and closes the water feed conduit 43, and a water filter 44 that filters water. The water supply source connection portion 46 is connected, for example, through a hose, with a water supply source 49 such as plumbing that delivers water.

A diluting valve 47 is provided in the water feed conduit 43 between the water filter 44 and the three-way valve 42. The diluting conduit 48 that makes the diluting valve 47 communicate with the medicinal solution tank 20 is connected with the diluting valve 47. The diluting valve 47 can be switched among a state of making the water filter 44 communicate with the three-way valve 42 and a state of making the water filter 44 communicate with the diluting conduit 48. The three-way valve 42, the water lead-in valve 45, and the diluting valve 47 are connected with the control section 5, and the motion of these valves is controlled by the control section 5.

When the three-way valve 42 is put into the state of making the circulation nozzle 14 communicate with the treatment tank circulation conduit 40, the diluting valve 47 is put into the state of making the water filter 44 communicate with the three-way valve 42, and the operation of the liquid flowing pump 41 is started while the liquid is reserved in the treatment tank 2, the liquid in the treatment tank 2 is ejected from the circulation nozzle 14 through the circulation port 13, the circulation conduit 13a, and the treatment tank circulation conduit 40.

Also, when the three-way valve 42 is put into the state of making the circulation nozzle 14 communicate with the water feed conduit 43, the diluting valve 47 is put into the state of making the water filter 44 communicate with the three-way valve 42, and the water lead-in valve 45 is open, water supplied from the water supply source 49 is ejected from the circulation nozzle 14. The liquid ejected from the circulation nozzle 14 is led into the treatment tank 2.

Further, when the diluting valve 47 is put into the state of making the water filter 44 communicate with the diluting conduit 48 and the water lead-in valve 45 is open, the water supplied from the water supply source 49 is led into the medicinal solution tank 20.

The cleaning liquid nozzle 15 is an opening portion that communicates, through a cleaning liquid conduit 51, with a cleaning liquid tank 50 that reserves the cleaning liquid. The cleaning liquid is used for the cleaning treatment. The cleaning liquid conduit 51 is provided with a cleaning liquid pump 52. The cleaning liquid pump 52 is connected with the control section 5, and the motion of the cleaning liquid pump 52 is controlled by the control section 5. Operating the cleaning liquid pump 52 causes the cleaning liquid in the cleaning liquid tank 50 to be transferred to the treatment tank 2.

The first water level sensor 60 is disposed in the treatment tank 2, and detects whether a height of a liquid surface of the liquid reserved in the treatment tank 2 is equal to or higher than a predetermined water level L1. The water level sensor 60 is electrically connected with the control section 5, and provides information of a detection result to the control section 5.

The configuration of the first water level sensor 60 is not particularly limited. The first water level sensor 60 may be of a so-called floating type water level sensor that detects whether the height of the liquid surface of the liquid is equal to or higher than the predetermined water level L1, based on a motion state of a switch. The switch opens and closes in response to vertical movement of a float that floats on the liquid reserved in the treatment tank 2. Also, for example, the first water level sensor 60 may be of a so-called electrode type water level sensor that includes a plurality of electrodes separately disposed and detects whether the height of the liquid surface of the liquid is equal to or higher than the predetermined water level L1, based on presence or absence of electrical conduction between the plurality of electrodes. The electrical conduction is varied based on whether the plurality of electrodes have sunk in the liquid.

The predetermined water level L1 is set to a position higher than the highest portion of the plurality of endoscopes disposed inside the treatment tank 2. In other words, when the liquid is reserved in the treatment tank 2 up to the predetermined water level L1, all of the endoscopes disposed inside the treatment tank 2 wholly sink in the liquid.

The endoscope information reading section 9 reads endoscope information from the endoscope, and transmits the endoscope information to the control section 5. The endoscope information includes information of identifiers that are provided to the respective endoscopes. Each of the identifiers may be determined by a manufacturer of the endoscope or may be uniquely determined by the user of the endoscope.

The method in which the endoscope information reading section 9 reads the endoscope information from the endoscope is not particularly limited. In the present embodiment, as an example, the endoscope information is stored in an RFID tag incorporated in or attached to the endoscope, and the endoscope information reading section 9 is an RFID tag reader that reads the endoscope information from the RFID tag.

Note that the endoscope information may be displayed on an outer surface of the endoscope or the tag attached to the endoscope, by characters, a barcode, a two-dimensional code, or the like. The endoscope information reading section 9 may be an apparatus that recognizes the characters, the barcode, or the two-dimensional code to read the endoscope information. Further, the endoscope information reading section 9 may be provided in the electronic apparatus that is separated from the main body section 1a of the endoscope reprocessor 1 and performs wired communication or wireless communication with the control section 5.

The control section 5 stores, in a memory section 5a, the endoscope information read from the endoscope by the endoscope information reading section 9. Note that the memory section 5a may be included in the control section 5 or may be separated from the control section 5. The endoscope information is associated with history information and is stored as management information. The history information includes information such as a date on which the reprocessing is performed by the endoscope reprocessor 1.

Note that the endoscope information reading section 9 may read information of an identifier provided to the user. In this case, the control section 5 associates the identifier of the user, the endoscope information, and the history information with one another and stores the information in the memory section 5a.

The determination section 10 determines whether a first number N1 is equal to a second number N2. The first number N1 is the number of endoscopes, the endoscope information of which are read by the endoscope information reading section 9. The second number N2 is the number of endoscopes disposed in the treatment tank 2, detected by the number detection section 80 described later. Note that the determination section 10 may be included in the control section 5, or may be separated from the control section 5 and provide information of the determination result to the control section 5.

The number detection section 80 detects the second number N2 that is the number of endoscopes disposed inside the treatment tank 2, and transmits the information of the second number N2 to the control section 5. The detailed configuration of the number detection section 80 is described later.

Figure 2:
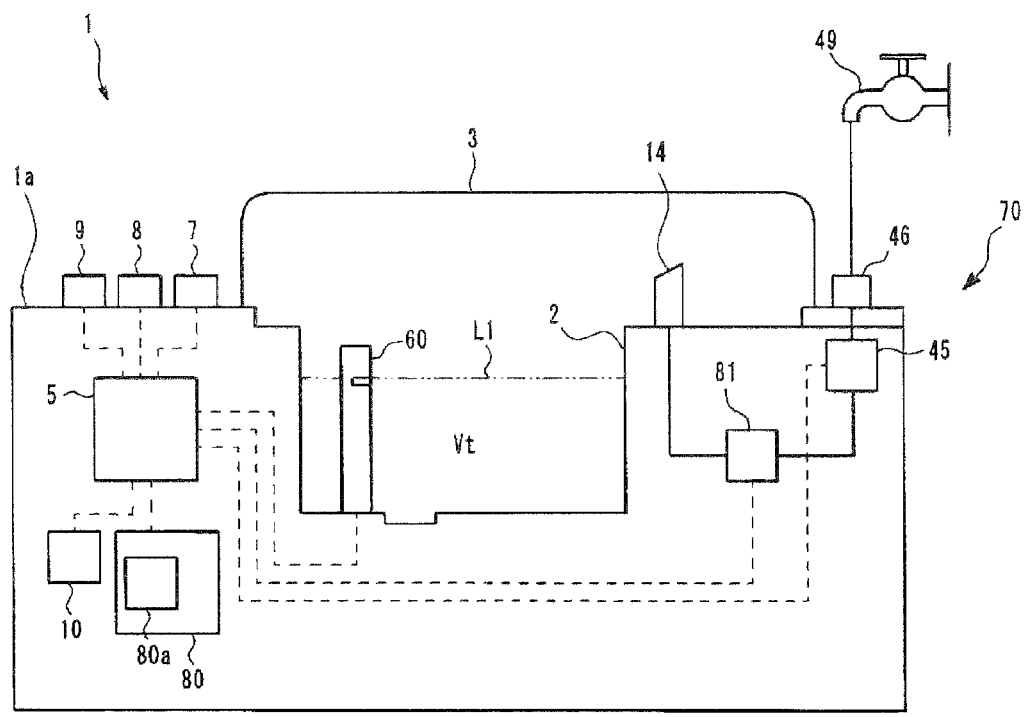
FIG. 2 is a diagram illustrating a configuration relating to a number detection section according to the first embodiment.

FIG. 2 is a diagram illustrating a configuration relating to the number detection section 80 according to the present embodiment. The number detection section 80 includes a first calculation section 80a. The first calculation section 80a calculates the second number N2 that is the number of endoscopes disposed inside the treatment tank 2, based on a lead-in amount Vi. The lead-in amount Vi is a volume of the liquid led into the treatment tank 2 from a state in which no liquid is reserved in the treatment tank 2 until the liquid is led into the treatment tank 2 and the liquid surface of the liquid reserved in the treatment tank 2 reaches the predetermined water level L1. Note that the number detection section 80 may be included in the control section 5, or may be separated from the control section 5 and provide information of the detection result of the second number N2 to the control section 5.

The liquid, the lead-in amount Vi of which is to be measured, is supplied into the treatment tank 2 by a liquid supply section 70. A kind of the liquid, the lead-in amount Vi of which is to be measured, is not particularly limited as long as the liquid is suppliable by an amount sufficient to fill the treatment tank 2 up to the predetermined water level L1.

In the present embodiment, as an example, the liquid, the lead-in amount Vi of which is to be measured, is water supplied from the external water supply source 49 of the endoscope reprocessor 1. In other words, the liquid supply section 70 of the present embodiment includes the water supply source connection portion 46, the water lead-in valve 45, and the water feed conduit 43.

Note that the liquid, the lead-in amount Vi of which is to be measured, may be the liquid reserved in the endoscope reprocessor 1. Examples of the liquid reserved in the endoscope reprocessor 1 by an amount sufficient to fill the treatment tank 2 up to the predetermined water level L1 may include the medicinal solution reserved in the medicinal solution tank 20.

The configuration to measure the lead-in amount Vi of the liquid led into the treatment tank 2 is not particularly limited. In the present embodiment, as an example, the endoscope reprocessor 1 includes a flowrate sensor 81 that measures a flowrate of the liquid supplied from the liquid supply section 70 to the treatment tank 2, and measures the lead-in amount Vi with use of the flowrate sensor 81.

In the present embodiment in which the liquid supply section 70 leads the water supplied from the water supply source 49, into the treatment tank 2, the flowrate sensor 81 is provided in the water feed conduit 43, and measures the flowrate of the water flowing through the water feed conduit 43. Note that the flowrate sensor 81 may be provided in the circulation nozzle 14 or the water supply source connection portion 46.

The flowrate sensor 81 is electrically connected with the control section 5, and transmits information of the measurement result to the control section 5. Note that it is sufficient for the flowrate sensor 81 to measure a value necessary for allowing the control section 5 to acquire the lead-in amount Vi. For example, the flowrate sensor 81 may output, as the measurement result, the volume of the liquid led into the treatment tank 2 in a period specified by the control section 5, or for example, the flowrate sensor 81 may output, as the measurement result, information of the volume of the liquid led into the treatment tank 2 per unit time period. Alternatively, for example, the flowrate sensor 81 may output, as the measurement result, information of flow velocity or pressure in a predetermined segment of the conduit through which the liquid flows. In any case, it is well-known that the control section 5 can obtain the lead-in amount Vi, based on the measurement result of the flowrate sensor 81.

The control section 5 provides, to the first calculation section 80a of the number detection section 80, the value of the lead-in amount Vi obtained based on the measurement result of the flowrate sensor 81.

Since the lead-in amount Vi typically decreases as the number of endoscopes disposed inside the treatment tank 2 increases, the first calculation section 80a can calculate, from the lead-in amount Vi, the number of endoscopes disposed inside the treatment tank 2.

For example, when the lead-in amount is lower than a predetermined value Vi1, the number of endoscopes disposed inside the treatment tank 2 is calculated as two. When the lead-in amount is equal to or higher than the predetermined value Vi1, the number of endoscopes disposed inside the treatment tank 2 is calculated as one.

The determination section 10 compares the first number that is the number of endoscopes read by the endoscope information reading section 9 with the second number that is the number of endoscopes calculated by the first calculation section 80a, thereby determines whether the first number is equal to the second number.

When the determination section 10 determines that the first number is different from the second number, the control section 5 drives the notification section 8 to notify the user of the result.

For example, in a case where the first number is one and the second number is two, this indicates that, although information of only one endoscope has been read by the endoscope information reading section 9, two endoscopes are disposed inside the treatment tank 2.

Note that, in FIG. 2, the number detection section 80 is connected with the determination section 10 through the control section 5; however, the number detection section 80 may be directly connected with the determination section 10.

The following precise determination method may be adopted as a first modification of the present embodiment. The first calculation section 80a included in the number detection section 80 acquires a volume Ve(n) of the endoscope corresponding to the endoscope information that has been read by the endoscope information reading section 9 and stored in the memory section 5a. In this case, n is a number provided to an individual piece of endoscope information for description and is an integer of one or larger. For example, when the endoscope information of two endoscopes have been read by the endoscope information reading section 9 and stored, a volume of the endoscope corresponding to a first piece of the endoscope information is Ve(1) and a volume of the endoscope corresponding to a second piece of the endoscope information is Ve(2). The maximum value of the number n is equivalent to the first number N1.

Note that the value of the volume Ve is not necessarily equivalent to the volume of the individual endoscope, and may be an approximate value.

The configuration in which the first calculation section 80*a* acquires the volume of the endoscope corresponding to the endoscope information is not particularly limited. For example, the information of the value of the volume Ve may be directly included in the endoscope information, and the first calculation section 80*a* may read the endoscope information to acquire the volume Ve(n) of the endoscope.

Alternatively, for example, the endoscope information may include information necessary for calculating the value of the volume Ve(n), and the first calculation section 80*a* may calculate the volume Ve(n) of the endoscope based on the endoscope information. In this case, for example, the endoscope information may include information indicating a type (a model name) of the endoscope, and the number detection section 80 calculates the value of the volume Ve(n) from the endoscope information with use of a reference table that is previously stored and indicates relationship between the type and the volume Ve(n) of the endoscope. Note that the endoscope information may preferably include information of a length and an outer shape of an insertion portion and the like because the information allows the first calculation section 80*a* to more accurately calculate the volume Ve(n) of the endoscope.

In the present embodiment, as mentioned above, two endoscopes at maximum are arrangeable inside the treatment tank 2. Therefore, for example, when the endoscope information of the two endoscopes has been read by the endoscope information reading section 9 and stored (when the first number N1 is two), the first calculation section 80*a* acquires the volumes Ve(1) and Ve(2) of the respective two endoscopes. Alternatively, for example, when the endoscope information of one endoscope has been read and stored (when the first number N1 is one), the first calculation section 80*a* acquires the volume Ve(1) of the endoscope.

Thereafter, the first calculation section 80*a* calculates a total volume Vea that is a total sum of the volumes Ve(n) of all of the endoscopes, the endoscope information of which has been read by the endoscope information reading section 9.

In the present embodiment, for example, when the first number N1 is two, an equation of Vea=Ve(1)+Ve(2) is established. Also, for example, when the first number N1 is one, an equation of Vea=Ve(1) is established.

Further, the first calculation section 80*a* holds a capacity Vt up to the predetermined water level L1 of the treatment tank 2. The capacity Vt is a preset fixed value. In other words, the capacity Vt is a volume of the liquid necessary to fill the treatment tank 2 up to the predetermined water level L1 in the case where no endoscope is disposed inside the treatment tank 2.

The first calculation section 80*a* calculates a volume difference Vd that is a value obtained by subtracting the lead-in amount Vi from the capacity of the treatment tank Vt. The volume difference Vd is substantially equal to a measured value of the total volume of all of the endoscopes disposed inside the treatment tank 2. In this case, the reason for "substantially equal" is because accessories of the endoscopes, a cleaning tube, and the like are disposed inside the treatment tank 2 in addition to the endoscopes, and the volumes of the accessories and the cleaning tube are also included in the value of the volume difference Vd.

If all of the endoscopes, the endoscope information of which has been read by the endoscope information reading section 9, are disposed inside the treatment tank 2, the value of the total volume Vea of the endoscopes predicted from the endoscope information approximates to the value of the volume difference Vd that is calculated from the lead-in amount Vi of the liquid actually led into the treatment tank 2.

Therefore, when the volume difference Vd is a value within a predetermined range relative to the total volume Vea, the first calculation section 80*a* calculates the second number N2 that is the number of endoscopes actually disposed inside the treatment tank 2, as the value same as the first number N1 that is the number of endoscopes, the endoscope information of which has been read by the endoscope information reading section 9.

In other words, when an absolute value of a difference between the total volume Vea and the volume difference Vd is equal to or lower than a predetermined value A, the first calculation section 80*a* makes the second number N2 equal to the first number N1. The predetermined value A is smaller than a value of the volume of the endoscope having the smallest volume out of the endoscopes that are processed by the endoscope reprocessor 1, and is a value allowing the measurement error of the volume difference Vd.

If the endoscopes of the number larger than one or more of endoscopes, the endoscope information of which has been read by the endoscope information reading section 9, are disposed inside the treatment tank 2, the value of the total volume Vea of the endoscopes predicted from the endoscope information becomes smaller than the value of the volume difference Vd that is calculated from the lead-in amount Vi of the liquid actually led into the treatment tank 2. The difference between the total volume Vea and the volume difference Vd in this case becomes a value close to or larger than the volume of one endoscope.

Accordingly, when the volume difference Vd is a value within a predetermined range relative to the total volume Vea, the first calculation section 80*a* calculates the second number N2 that is the number of endoscopes actually disposed inside the treatment tank 2, as a value larger than the first number N1 that is the number of endoscopes, the endoscope information of which has been read by the endoscope information reading section 9.

In the present embodiment, as mentioned above, two endoscopes at maximum are arrangeable inside the treatment tank 2. Therefore, for example, when two endoscopes are placed inside the treatment tank 2 after the endoscope information reading section 9 reads the endoscope information of one endoscope, the first number N1 is 1, and the first calculation section 80*a* calculates the second number N2 as two that is a value larger than the first number.

Alternatively, for example, when one endoscope is placed inside the treatment tank 2 without being subjected to endoscope information reading by the endoscope information reading section 9, the first number N1 is zero and the first calculation section 80*a* calculates the second number N2 as one or two that is value larger than the first number.

As mentioned above, the determination section 10 determines whether the first number N1 that is the number of endoscopes, the endoscope information of which has been read by the endoscope information reading section 9, is equal to the second number N2 that is the number of endoscopes disposed inside the treatment tank 2 detected by the number detection section 80.

The control section 5 drives the notification section 8 when the determination section 10 determines that the first number N1 is different from the second number N2. The determination section 10 determines that the first number N1 is different from the second number N2 when the number of endoscopes (the first number N1), the endoscope information of which has been read by the endoscope information reading section 9, is different from the number of endoscopes (the second number N2) disposed inside the treatment tank 2 detected by the number detection section 80, as mentioned above. In this case, one or the plurality of endoscopes disposed inside the treatment tank 2 includes an endoscope that has not been subjected to the endoscope information reading by the endoscope information reading section 9.

The control section 5 drives the notification section 8 to notify the user of an error in which an endoscope that has not been subjected to the endoscope information reading by the endoscope information reading section 9 is disposed inside the treatment tank 2.

Figure 3:
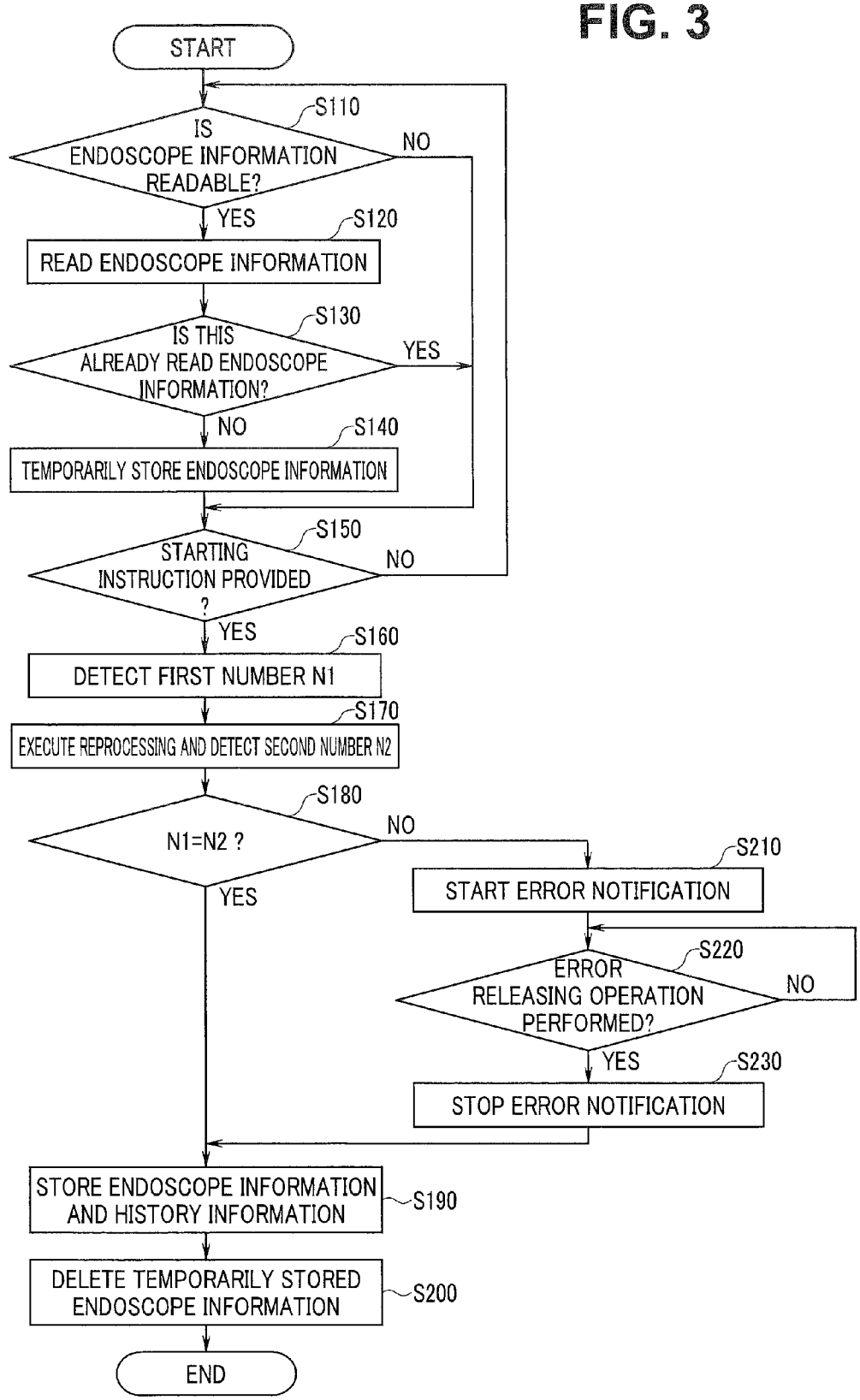
FIG. 3 is a flowchart illustrating operation of the endoscope reprocessor according to the first embodiment.

Next, the motion of the endoscope reprocessor 1 having the above-described configuration is described. FIG. 3 is a flowchart illustrating motion of the endoscope reprocessor 1.

First, in step S110, the control section 5 determines whether the endoscope information reading section 9 can read the endoscope information. For example, the endoscope information reading section 9 can read the endoscope information when the RFID tag incorporated in or attached to the endoscope is brought into a range readable by the endoscope information reading section 9.

When the endoscope information reading section 9 cannot read the endoscope information in step S110, the process proceeds to step S150.

On the other hand, when the endoscope information reading section 9 can read the endoscope information, the process proceeds to step S120.

In step S120, the control section 5 causes the endoscope information reading section 9 to read the endoscope information. Next, in step S130, the control section 5 determines whether the endoscope information read by the endoscope information reading section 9 has been already read and temporarily stored in the memory section 5a.

When it is determined in step S130 that the endoscope information has not been read, the control section 5 temporarily stores the endoscope information in the memory section 5a in step S140. When it is determined in step S130 that the endoscope information has been already read, the control section 5 skips step S140 and does not store the endoscope information.

In step S150, the control section 5 determines whether the starting instruction of the reprocessing from the user has been inputted through the operation section 7. When it is determined in step S150 that the starting instruction of the reprocessing has not been inputted, the process returns to step S110 and the control section 5 repeats the above-descried motion.

The user places the endoscopes inside the treatment tank 2, and then operates the operation section 7 to input the starting instruction of the reprocessing. When it is determined in step S150 that the starting instruction of the reprocessing has been inputted, the process proceeds to step S160.

In step S160, the control section 5 detects the first number N1 that is the number of endoscopes, the endoscope information of which has been read by the endoscope information reading section 9. The first number N1 is the number of the endoscopes corresponding to one or a plurality of pieces of endoscope information temporarily stored in the memory section 5a.

Next, in step S170, the control section 5 performs the reprocessing of the endoscopes disposed inside the treatment tank 2 and the detection processing of the second number N2.

Although the reprocessing motion of the endoscope reprocessor 1 is well-known and the detailed description of the reprocessing motion is accordingly omitted here, the reprocessing includes a process of leading the liquid such as water and medicinal solution into the treatment tank 2 up to the first water level L1 and immersing the endoscopes in the liquid.

When executing the process of leading the liquid into the treatment tank 2 up to the first water level L1, the control section 5 causes the number detection section 80 to detect the second number N2 described above. More specifically, in the present embodiment, when executing the process of leading the water into the treatment tank 2 up to the first water level L1 by the liquid supply section 70 from a state in which no liquid is reserved in the treatment tank 2, the control section 5 drives the flowrate sensor 81 to acquire the lead-in amount Vi that is a volume of the water led into the treatment tank 2.

Then, as mentioned above, the number detection section 80 calculates the total volume Vea that is the total sum of the volumes of one or the plurality of endoscopes corresponding to all pieces of the endoscope information temporarily stored in the memory section 5a, and detects the second number N2 that is the number of endoscopes actually disposed inside the treatment tank 2, based on the values of the total volume Vea, the lead-in amount Vi, and the capacity Vt of the treatment tank 2.

In this way, in the present embodiment, it is possible to detect the second number N2 by the number detection section 80 during the performing of the reprocessing.

Thereafter, in step S180, the control section 5 causes the determination section 10 to determine whether the first number N1 that is the number of endoscopes, the endoscope information of which has been read by the endoscope information reading section 9, is equal to the second number N2 that is the number of endoscopes disposed inside the treatment tank 2 detected by the number detection section 80. Note that step S180 may be performed during a performing period of the reprocessing or after the reprocessing is completed.

When it is determined in step S180 that the first number N1 is equal to the second number N2, the process proceeds to step S190 after completion of the reprocessing. In step S190, the control section 5 associates the endoscope information temporarily stored, with the history information including information of the date on which the reprocessing is performed and the like, and stores the associated information as new management information in the memory section 5a. Thereafter, in step S200, the control section 5 deletes the endoscope information temporarily stored.

On the other hand, when it is determined in step S180 that the first number N1 is different from the second number N2, the process proceeds to step S210. In step S210, the control section 5 drives the notification section 8 to start error notification. The error notification notifies occurrence of an error in which an endoscope that has not been subjected to the endoscope information reading by the endoscope information reading section 9 is disposed inside the treatment tank 2. For example, in step S210, generation of warning sound from the notification section 8 is started. Step S210 may be executed during the performing period of the reprocessing or after the reprocessing is completed.

Thereafter, in step S220, the control section 5 determines whether an error releasing operation is performed by the user. The control section 5 waits until the user performs the error releasing operation, and when the error releasing operation is performed, the control section 5 stops the error notification in step S230. In other words, the control section 5 drives the notification section 8 to continue the error notification until the error releasing operation is performed.

The error releasing operation indicates that, for example, the user inputs instruction to stop the error notification through the operation section 7. Note that the error releasing operation may indicate that the user causes the endoscope information reading section 9 to read the endoscope information of the endoscope that has not been subjected to the endoscope information reading.

After the error notification is stopped, the process proceeds to step S190, and the control section 5 associates the endoscope information temporarily stored with the history information including the information of the date on which the reprocessing is performed and the like, and stores the associated information as new management information in the memory section 5a. Then, in step S200, the control section 5 deletes the endoscope information temporarily stored.

As mentioned above, the endoscope reprocessor 1 according to the present embodiment includes: the endoscope information reading section 9 configured to read the endoscope information from each of the endoscopes; the treatment tank 2 in which the endoscopes are disposed; the number detection section 80 configured to detect the number of endoscopes disposed inside the treatment tank 2; the determination section 10 configured to determine whether the first number N1 that is the number of endoscopes read by the endoscope information reading section 9 is equal to the second number N2 that is the number of endoscopes detected by the number detection section 80; the notification section 8 configured to execute the error notification; and the control section 5 that is connected with the determination section 10 and the notification section 8 and drives the notification section 8 when the determination section 10 determines that the first number N1 is different from the second number N2.

The endoscope reprocessor 1 according to the present embodiment including such a configuration causes the notification section 8 to execute the error notification when the first number N1 is different from the second number N2, namely, when the endoscope that has not been subjected to the endoscope information reading by the endoscope information reading section 9 is disposed inside the treatment tank 2. Therefore, in the endoscope reprocessor 1 according to the present embodiment, it is possible to prevent forgetting of the endoscope information reading by the endoscope information reading section 9.

Moreover, in the present embodiment, the number detection section 80 detects the second number N2, based on the lead-in amount Vi of the liquid that fills the treatment tank 2 up to the predetermined water level L1 in the reprocessing. In other words, in the present embodiment, the detection motion of the second number N2 by the number detection section 80 is executed simultaneously with the reprocessing. Therefore, a waiting time period for execution of the detection motion of the second number N2 does not occur.

In the endoscope reprocessor 1 according to the present embodiment described above, the liquid supply section 70 leads water into the treatment tank 2, and the number detection section 80 detects the second number N2 based on the measurement result of the lead-in amount Vi of the water into the treatment tank 2. The liquid, the lead-in amount Vi of which is to be measured, however, is not limited to water. For example, the liquid, the lead-in amount Vi of which is to be measured, may be the medicinal solution reserved in the medicinal solution tank 20.

Figure 4:
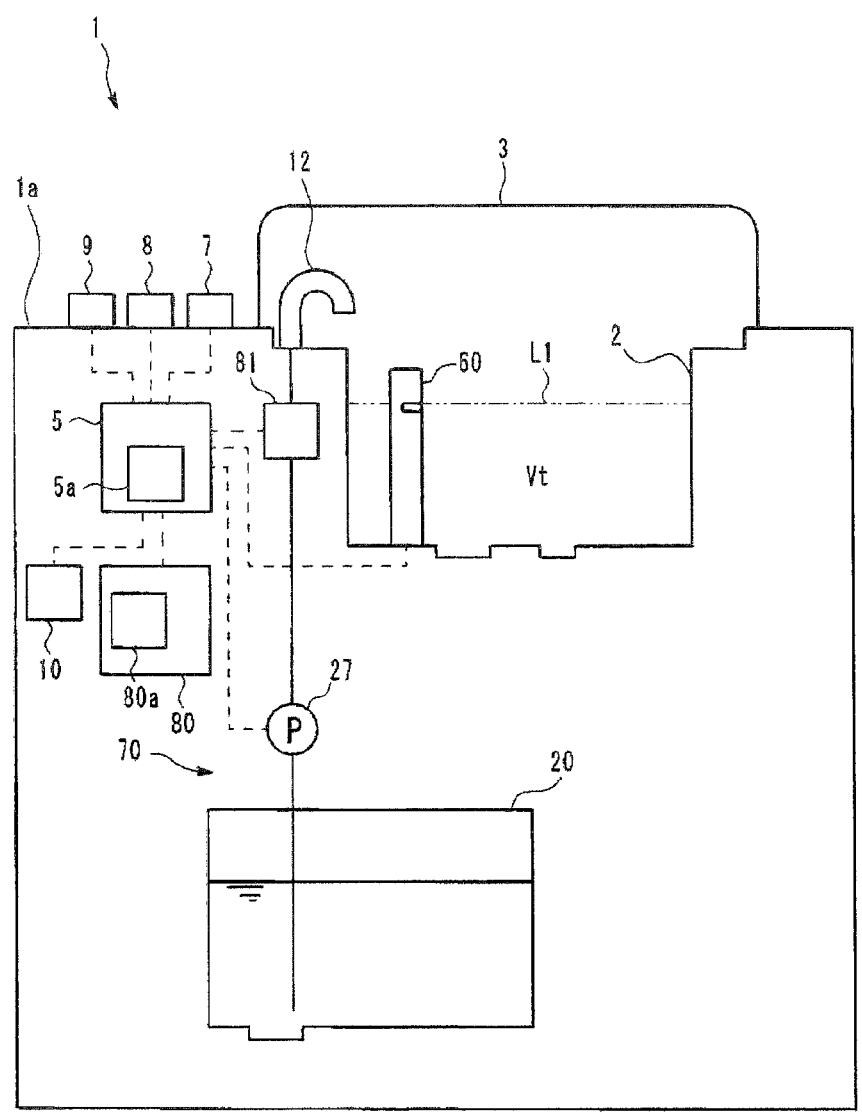
FIG. 4 is a diagram illustrating a configuration relating to a number detection section of an endoscope reprocessor according to a second modification of the first embodiment.

FIG. 4 is a diagram illustrating a second modification of the present embodiment. In the second modification illustrated in FIG. 4, the liquid supply section 70 leads the medicinal solution into the treatment tank 2, and the number detection section 80 detects the second number N2 based on the measurement result of the lead-in amount Vi of the medicinal solution led into the treatment tank 2 by the liquid supply section 70.

As illustrated in FIG. 4, the liquid supply section 70 according to the present modification includes the medicinal solution conduit 26 and the medicinal solution pump 27. The medicinal solution conduit 26 makes the medicinal solution tank 20 that reserves the medicinal solution, communicate with the treatment tank 2. The medicinal solution pump 27 is provided in the medicinal solution conduit 26. The medicinal solution conduit 26 is provided with the flowrate sensor 81. The control section 5 acquires the lead-in amount Vi based on the measurement result of the flowrate sensor 81, and provides the value of the lead-in amount Vi to the number detection section 80.

Also in the endoscope reprocessor 1 according to the present modification described above, the notification section 8 executes the error notification when the first number N1 is different from the second number N2, which makes it possible to prevent forgetting of the endoscope information reading by the endoscope information reading section 9.

Further, similarly to the above-described embodiment, the number detection section 80 detects the second number N2 at the same time when the process of filling the treatment tank 2 up to the predetermined water level L1 with the medicinal solution is executed in the reprocessing. Therefore, since the detection motion of the second number N2 by the number detection section 80 is executed simultaneously with the reprocessing also in the present modification, the waiting time period for execution of the detection motion of the second number N2 does not occur.

Moreover, in the endoscope reprocessor 1 according to the present embodiment described above, the lead-in amount Vi of the liquid into the treatment tank 2 by the liquid supply section 70 is measured with use of the flowrate sensor 81. The method of measuring the lead-in amount Vi, however, is not limited to the method using the flowrate sensor 81.

Figure 5:
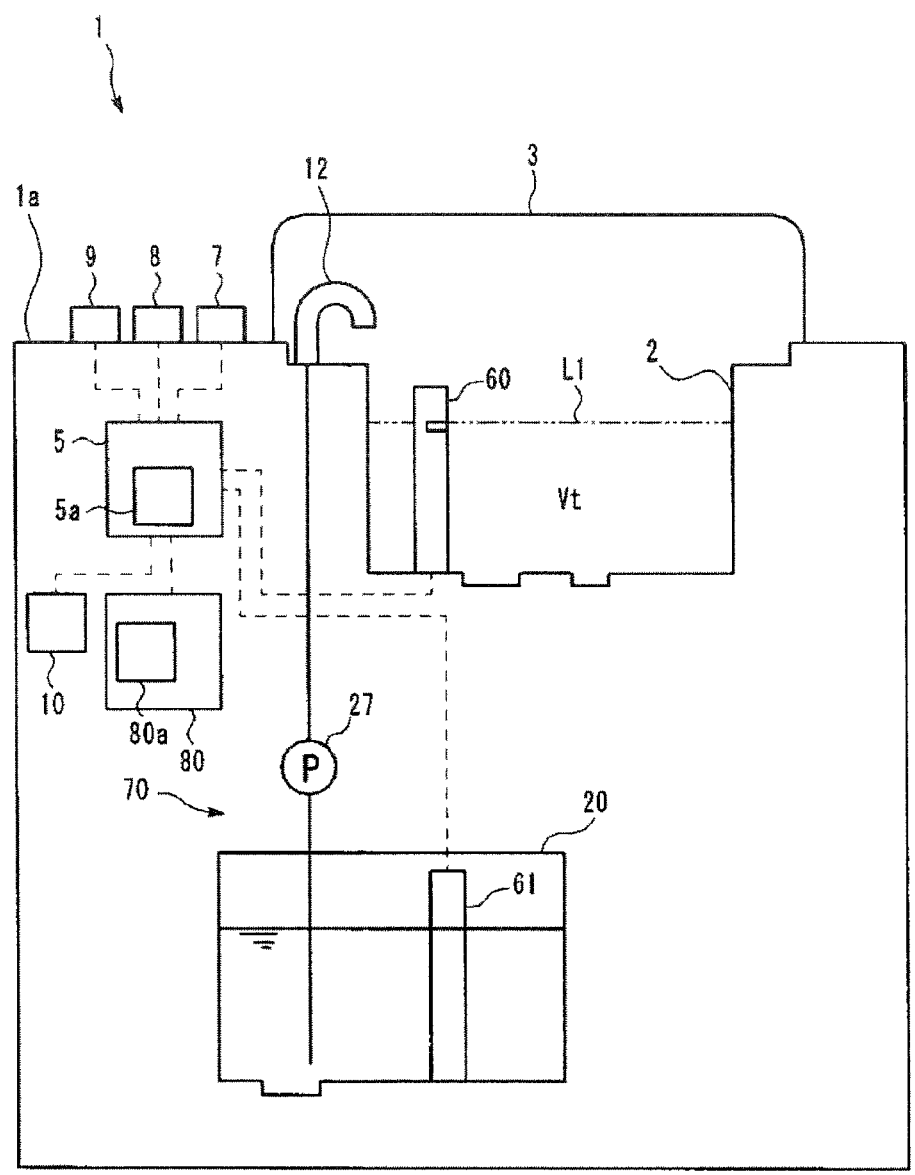
FIG. 5 is a diagram illustrating a configuration relating to a number detection section of an endoscope reprocessor according to a third modification of the first embodiment.

FIG. 5 is a diagram illustrating a third modification of the present embodiment. In the third modification illustrated in FIG. 5, the liquid supply section 70 leads, into the treatment tank 2, the medicinal solution reserved in the medicinal solution tank 20. Further, the medicinal solution tank 20 according to the present modification is provided with a second water level sensor 61 that measures variation of a height of a solution surface of the medicinal solution in the medicinal solution tank 20. The second water level sensor 61 is electrically connected with the control section 5, and provides a measurement result to the control section 5.

The control section 5 according to the present modification calculates a decrement of the medicinal solution that is a volume of the medicinal solution led out from the medicinal solution tank 20 by the liquid supply section 70, based on the variation of the height of the liquid surface of the medicinal solution in the medicinal solution tank 20 detected by the second water level sensor 61 and information of a shape of the medicinal solution tank 20 that is previously provided. The decrement indicates the lead-in amount Vi of the medicinal solution led into the treatment tank 2 by the liquid supply section 70.

The control section 5 provides, to the number detection section 80, the value of the decrement of the medicinal solution that is led out from the medicinal solution tank 20 by the liquid supply section 70. The number detection section 80 detects the second number N2, based on the measurement result of the decrement of the medicinal solution that is led out from the medicinal solution tank 20 by the liquid supply section 70.

Also in the endoscope reprocessor 1 according to the present modification described above, the notification section 8 executes the error notification when the first number N1 is different from the second number N2, which makes it possible to prevent forgetting of the endoscope information reading by the endoscope information reading section 9.

Also, similarly to the above-described embodiment, the number detection section 80 detects the second number N2 at the same time when the process of filling the treatment tank 2 up to the predetermined water level L1 with the medicinal solution is executed in the reprocessing. Therefore, since the detection motion of the second number N2 by the number detection section 80 is executed simultaneously with the reprocessing also in the present modification, the waiting time period for execution of the detection motion of the second number N2 does not occur.

Second Embodiment

Next, a second embodiment of the present invention is described. In the following, only difference with the first embodiment is described, components similar to the components of the first embodiment are denoted by the same reference numerals, and description of the components is appropriately omitted.

Figure 6:
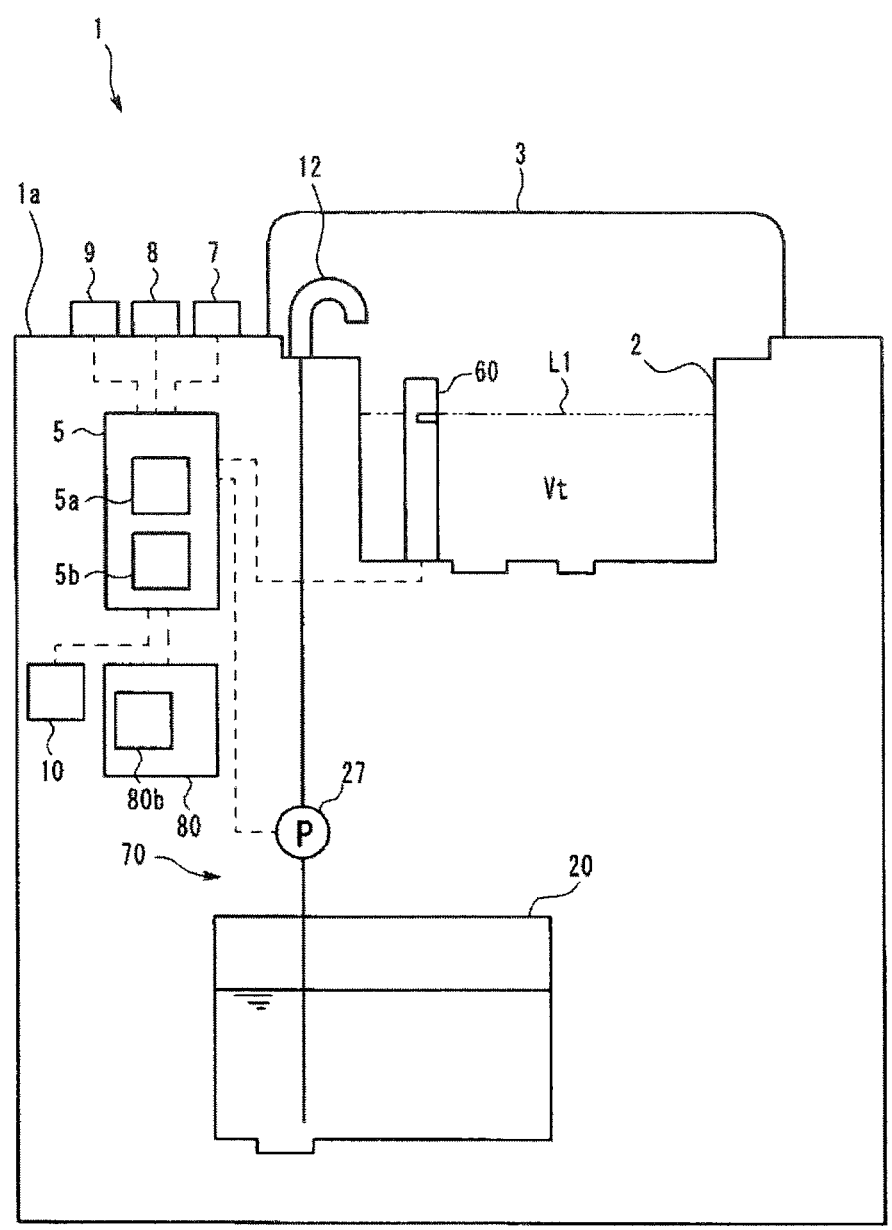
FIG. 6 is a diagram illustrating a configuration relating to a number detection section of an endoscope reprocessor according to a second embodiment.

FIG. 6 is a diagram illustrating a configuration relating to the number detection section 80 in the endoscope reprocessor 1 according to the present embodiment.

The endoscope reprocessor 1 according to the present embodiment includes the liquid supply section 70 that supplies liquid to the treatment tank 2 up to the predetermined water level L1. In the present embodiment, as an example, the liquid supply section 70 includes the medicinal solution conduit 26 and the medicinal solution pump 27. The medicinal solution conduit 26 makes the medicinal solution tank 20 that reserves the medicinal solution, communicate with the treatment tank 2. The medicinal solution pump 27 is provided in the medicinal solution conduit 26. The medicinal solution pump 27 transfers the medicinal solution that is liquid, at a constant flowrate when being driven.

Also, the endoscope reprocessor 1 according to the present embodiment includes a clocking section 5b that measures a time period T from a state in which no liquid is reserved in the treatment tank 2 until the liquid is led into the treatment tank 2 by the liquid supply section 70 and the liquid surface of the supplied liquid reaches the predetermined water level L1. The clocking section 5b may be included in or separated from the control section 5. The clocking section 5b provides a measurement result of the time period T to a second calculation section 80b of the number detection section 80.

More specifically, in the present embodiment, the clocking section 5b measures the time period T from a time point when the medicinal solution pump 27 is started to be driven in the state in which the liquid is not reserved in the treatment tank 2 until a time point when a liquid surface of the medicinal solution in the treatment tank 2 reaches the predetermined water level L1.

The second calculation section 80b of the number detection section 80 calculates, from the value of the time period T, the second number N2 that is the number of the endoscopes disposed inside the treatment tank 2.

Since the transferred amount of the medicinal solution per unit time period by the medicinal solution pump 27 is fixed, the lead-in amount Vi that is the volume of the medicinal solution led into the treatment tank 2 by the liquid supply section 70 is proportional to the time period T. In other words, the value of the time period T varies in response to change of the volumes of the endoscopes actually disposed inside the treatment tank 2.

Therefore, the second calculation section 80b included in the number detection section 80 according to the present embodiment calculates the lead-in amount Vi from the time period T, and calculates the second number N2 that is the number of endoscopes disposed inside the treatment tank 2, based on the lead-in amount Vi, as with the first embodiment.

Also in the endoscope reprocessor 1 according to the present embodiment mentioned above, the notification section 8 executes the error notification when the first number N1 is different from the second number N2, which makes it possible to prevent forgetting of the endoscope information reading by the endoscope information reading section 9, as with the first embodiment.

Moreover, as with the second modification of the first embodiment, the number detection section 80 according to the present embodiment detects the second number N2 at the same time when the process of filling the treatment tank 2 up to the predetermined water level L1 with the medicinal solution is executed in the reprocessing. Therefore, since the detection motion of the second number N2 by the number detection section 80 is executed simultaneously with the reprocessing also in the present embodiment, the waiting time period for execution of the detection motion of the second number N2 does not occur.

Third Embodiment

Next, a third embodiment of the present invention is described. In the following, only difference with the first embodiment is described, components similar to the components of the first embodiment are denoted by the same reference numerals, and description of the components is appropriately omitted.

Figure 7:
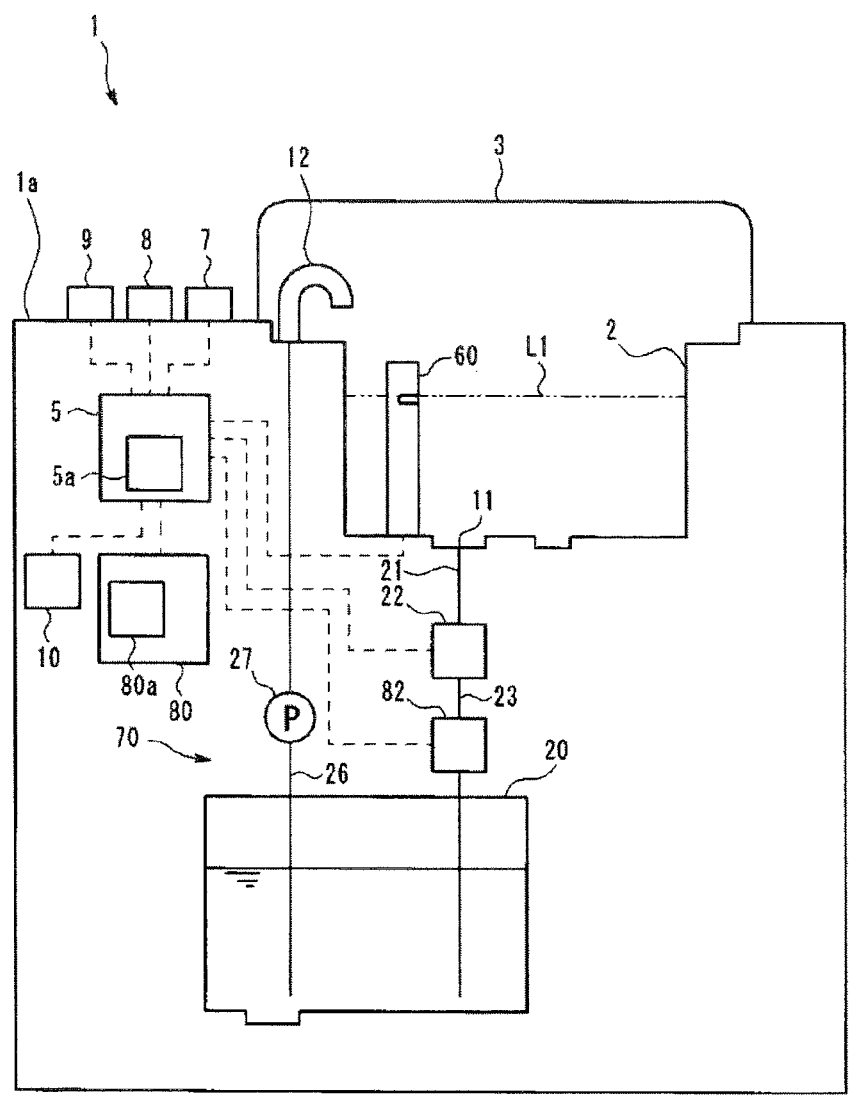
FIG. 7 is a diagram illustrating a configuration relating to a number detection section of an endoscope reprocessor according to a third embodiment.

FIG. 7 is a diagram illustrating a configuration relating to the number detection section 80 in the endoscope reprocessor 1 according to the present embodiment.

As mentioned above, in the first embodiment, the first calculation section 80a of the number detection section 80 calculates the second number N2 that is the number of endoscopes disposed inside the treatment tank 2, based on the lead-in amount Vi of the liquid led into the treatment tank 2 by the liquid supply section 70.

In contrast, the first calculation section 80a of the present embodiment calculates the second number N2 that is the number of endoscopes disposed inside the treatment tank 2, based on a measurement result of a discharge amount Vo that is a volume of the liquid discharged from the treatment tank 2 from a state in which the liquid is reserved in the treatment tank 2 up to the predetermined water level L1 to a state in which the liquid is not reserved in the treatment tank 2.

The endoscope reprocessor 1 according to the present embodiment includes a flowrate sensor 82 that measures a flowrate of liquid discharged from the treatment tank 2. The flowrate sensor 82 is electrically connected with the control section 5, and provides a measurement result to the control section 5.

In the present embodiment, as an example, the flowrate sensor 82 is provided in the recovery conduit 23 that makes the treatment tank 2 communicate with the medicinal solution tank 20 serving as the medicinal solution recovery section. As described in the first embodiment, the medicinal solution transferred from the medicinal solution tank 20 to the treatment tank 2 during the performing of the reprocessing is returned from the treatment tank 2 to the medicinal solution tank 20 through the recovery conduit 23 for reuse.

The control section 5 calculates the discharge amount Vo of the medicinal solution when all amount of the medicinal solution is discharged from the predetermined water level L1 of the treatment tank 2, based on the measurement result of the flowrate sensor 82, in the process of returning the medicinal solution from the treatment tank 2 to the medicinal solution tank 20 executed during the reprocessing. The discharge amount Vo is equivalent to the lead-in amount Vi of the medicinal solution that is led in to the treatment tank 2 by the liquid supply section 70 to fill the treatment tank 2 up to the predetermined water level L1 with the medicinal solution.

The control section 5 provides the value of the discharge amount Vo to the number detection section 80. The first calculation section 80a of the number detection section 80 detects the second number N2 based on the discharge amount Vo, namely, the lead-in amount Vi, as with the first embodiment.

Also in the endoscope reprocessor 1 according to the present embodiment described above, the notification section 8 executes the error notification when the first number N1 is different from the second number N2, which makes it possible to prevent forgetting of the endoscope information reading by the endoscope information reading section 9, as with the first embodiment.

Also, the number detection section 80 according to the present embodiment detects the second number N2 at the same time when the process of discharging all amount of the medicinal solution from the state in which the treatment tank 2 is filled with the medicinal solution up to the predetermined water level L1 is executed in the reprocessing. Therefore, since the detection motion of the second number N2 by the number detection section 80 is executed simultaneously with the reprocessing also in the present embodiment, the waiting time period for execution of the detection motion of the second number N2 does not occur.

In the endoscope reprocessor 1 according to the present embodiment described above, the second number N2 that is the number of endoscopes disposed inside the treatment tank 2 is calculated based on the measurement result of the discharge amount Vo of the medicinal solution that is discharged from the treatment tank 2 to the medicinal solution tank 20.

The measurement object of the discharge amount Vo, however, is not limited to the medicinal solution discharged from the treatment tank 2 to the medicinal solution tank 20. For example, the measurement object of the discharge amount Vo may be a liquid that is discharged from the treatment tank 2 to the outside of the endoscope reprocessor 1 through the discarding conduit 25.

Figure 8:
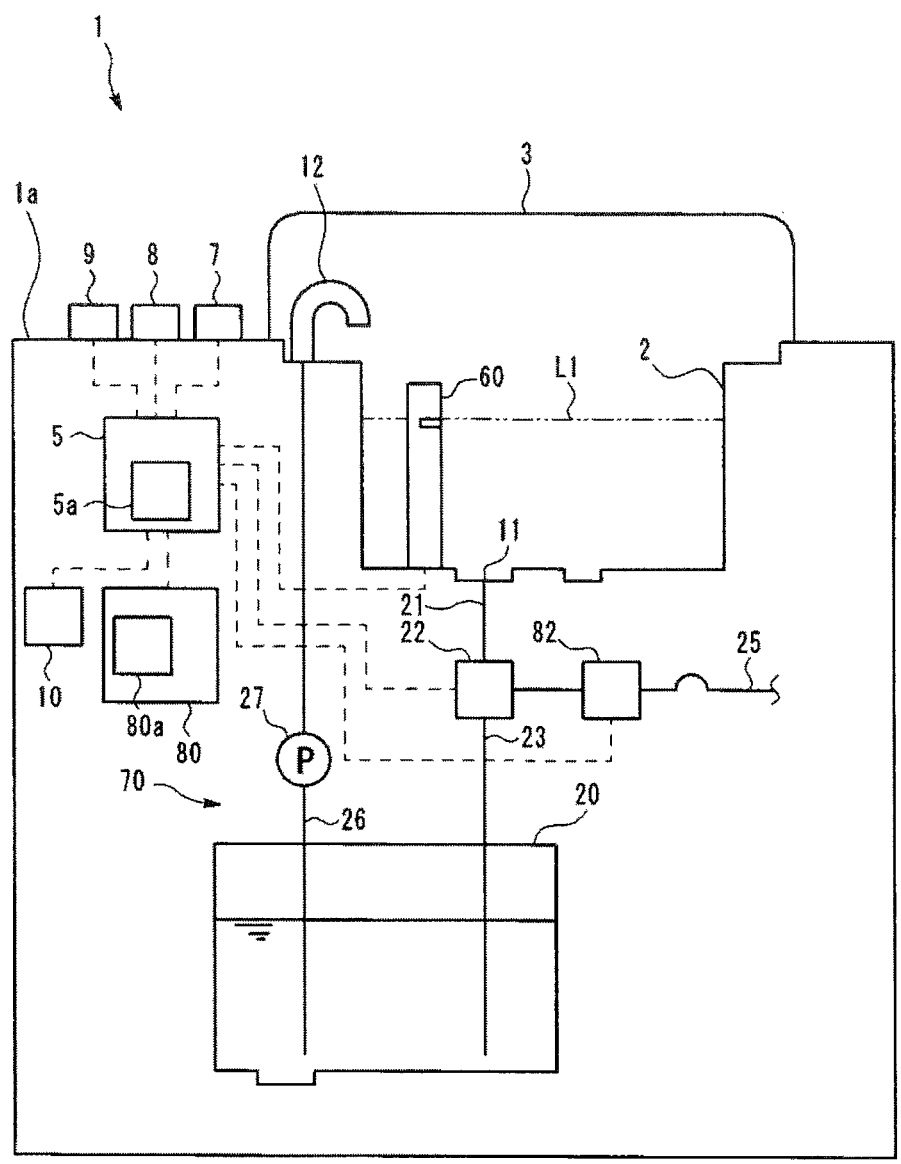
FIG. 8 is a diagram illustrating a configuration relating to a number detection section of an endoscope reprocessor according to a modification of the third embodiment.

FIG. 8 is a diagram illustrating a modification of the present embodiment. In the modification illustrated in FIG. 8, the flowrate sensor 82 is provided in the discarding conduit 25.

The control section 5 calculates the discharge amount Vo of the liquid when all amount of the liquid is discharged from the predetermined water level L1 of the treatment tank 2, based on the measurement result of the flowrate sensor 82, in the process of discharging the liquid such as water to the outside of the apparatus from the treatment tank 2 through the discarding conduit 25 executed during the reprocessing. Then, the first calculation section 80a of the number detection section 80 detects the second number N2 based on the discharge amount Vo, namely, the lead-in amount Vi, as with the first embodiment.

Also in the endoscope reprocessor 1 according to the present modification mentioned above, the notification section 8 executes the error notification when the first number N1 is different from the second number N2, which makes it possible to prevent forgetting of the endoscope information reading by the endoscope information reading section 9.

Further, similarly to the above-described embodiment, the number detection section 80 detects the second number N2 at the same time when the process of discharging all amount of the liquid from the state in which the treatment tank 2 is filled up to the predetermined water level L1 is executed in the reprocessing. Therefore, since the detection motion of the second number N2 by the number detection section 80 is executed simultaneously with the reprocessing, as with the first embodiment also in the present embodiment, the waiting time period for execution of the detection motion of the second number N2 does not occur.

Fourth Embodiment

Next, a fourth embodiment of the present invention is described. In the following, only differences with the first to third embodiments are described, components similar to the components of the first to third embodiments are denoted by the same reference numerals, and description of the components is appropriately omitted.

The endoscope reprocessor 1 according to the present embodiment is different from the above-described embodiments in the error releasing operation input determination process in step S220 in the flowchart illustrated in FIG. 3.

Figure 9:
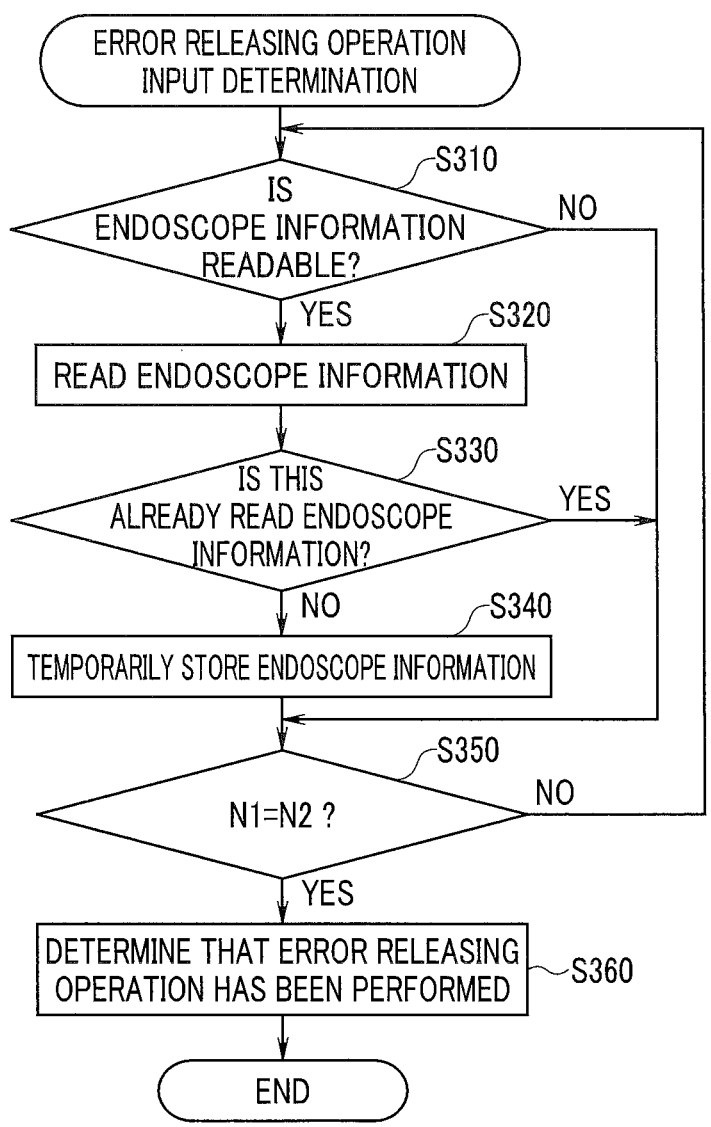
FIG. 9 is a flowchart of an error releasing operation input determination process of an endoscope reprocessor according to a fourth embodiment.

FIG. 9 is a flowchart of the error releasing operation input determination process of the endoscope reprocessor 1 according to the present embodiment. As described in the first embodiment, the control section 5 executes the error releasing operation input determination process illustrated in FIG. 9 after the notification section 8 starts the error notification. As described in the above-described first to third embodiments, the control section 5 causes the notification section 8 to start the error notification when the endoscope that has not been subjected to the endoscope information reading by the endoscope information reading section 9 is disposed inside the treatment tank 2, namely, when the first number N1 is different from the second number N2.

As illustrated in FIG. 9, in the error releasing operation input determination process according to the present embodiment, first, the control section 5 determines in step S310 whether the endoscope information reading section 9 can read the endoscope information. For example, the endoscope information reading section 9 can read the endoscope information when the RED tag incorporated in or attached to the endoscope is brought into a range readable by the endoscope information reading section 9.

When the endoscope information reading section 9 cannot read the endoscope information in step S310, the process proceeds to step S350.

On the other hand, when the endoscope information reading section 9 can read the endoscope information, the process proceeds to step S320. In step S320, the control section 5 causes the endoscope information reading section 9 to read the endoscope information.

Next, in step S330, the control section 5 determines whether the endoscope information read in step S320 is the already read endoscope information before the reprocessing and has been temporarily stored in the memory section 5a. In other words, the control section 5 determines whether endoscope information coincident with the endoscope information read in step S320 is included in the endoscope information that has been temporarily stored in the memory section 5a in the processes in steps S120 to S140 of FIG. 3.

When it is determined in step S330 that the endoscope information read in step S320 is not coincident with the endoscope information that has been already read before the reprocessing and has been temporarily stored in the memory section 5a, the process proceeds to step S340. In step S340, the control section 5 temporarily stores the endoscope information read in step S320 in the memory section 5a.

In other words, execution of step S340 increases the number of pieces of the endoscope information temporarily stored in the memory section 5a by one piece, and increases the value of the first number N1. After step S340 is executed, the process proceeds to step S350.

On the other hand, when it is determined in step S330 that the endoscope information read in step S320 is coincident with the endoscope information that has been already read before the reprocessing and has been temporarily stored in the memory section 5a, step S340 is skipped and the process proceeds to step S350.

In step S350, the control section 5 determines whether the first number N1 that is the number of endoscopes, the endoscope information of which has been read by the endoscope information reading section 9, is equal to the second number N2 that is the number of endoscopes disposed inside the treatment tank 2 detected by the number detection section 80 in step S170 of FIG. 3.

When the control section 5 determines in step S350 that the first number N1 is equal to the second number N2, the process proceeds to step S360. In step S360, the control section 5 determines that the error releasing operation has been performed by the user.

In other words, execution of step S360 results in determination of YES in step S220 of FIG. 3, the process then proceeds to step S230. In step S230, the control section 5 stops driving of the notification section 8, thereby stopping the error notification.

After execution of step S230, the process proceeds to step S190, and the control section 5 associates the endoscope information temporarily stored in the memory section 5a with the history information including information of the date on which the reprocessing is performed and the like, and stores the associated information as new management information in the memory section 5a. At this time, the number of pieces of endoscope information temporarily stored in the memory section 5a is equal to the second number N2 that is the number of endoscopes subjected to the reprocessing in the treatment tank 2. Accordingly, the endoscope reprocessor 1 according to the present embodiment makes it possible to accurately associate the endoscope information with the history information without omission. Thereafter, in step S200, the control section 5 deletes the endoscope information temporarily stored.

On the other hand, when the control section 5 determines in step S350 that the first number N1 is different from the second number N2, the process returns to step S310 and the processes from step S310 to step S350 mentioned above are repeated. The error notification by the notification section 8 is continued during the period in which the processes from step S310 to step S350 are repeated, because the determination of NO in step S220 of FIG. 3 continues.

As mentioned above, when the first number N1 that is the number of endoscopes, the endoscope information of which has been read by the endoscope information reading section 9, is different from the second number N2 that is the number of endoscopes disposed inside the treatment tank 2 detected by the number detection section 80, the endoscope reprocessor 1 according to the present embodiment starts to drive the notification section 8 to start the error notification motion. Thereafter, when the endoscope information of the endoscopes of the number equal to the second number N2 is read by the endoscope information reading section 9 (YES in step S350), the endoscope reprocessor 1 according to the present embodiment stops driving of the notification section 8.

As mentioned above, the endoscope reprocessor 1 according to the present embodiment continues the error notification until the number of pieces of the endoscope information temporarily stored in the memory section 5a becomes equal to the second number N2 that is the number of endoscopes subjected to the reprocessing in the treatment tank 2, thereby prompting the user to perform the endoscope information reading on the endoscope that has not been subjected to the endoscope information reading before the start of the reprocessing. Thus, according to the endoscope reprocessor 1 of the present embodiment, it is possible to prevent forgetting of the endoscope information reading by the endoscope information reading section 9, and to accurately associate the endoscope information with the history information without omission.

The other components of the endoscope reprocessor 1 according to the present embodiment are similar to the components of the first to third embodiments. Therefore, since the detection motion of the second number N2 by the number detection section 80 is executed simultaneously with the reprocessing also in the present embodiment, the waiting time period for execution of the second number N2 does not occur.

Fifth Embodiment

Next, a fifth embodiment of the present invention is described. In the following, only differences with the first to third embodiments are described, components similar to the components of the first to third embodiments are denoted by the same reference numerals, and description of the components is appropriately omitted.

The endoscope reprocessor 1 according to the present embodiment is different from the above-described embodiments in the error releasing operation input determination process in step S220 of the flowchart illustrated in FIG. 3.

Figure 10:
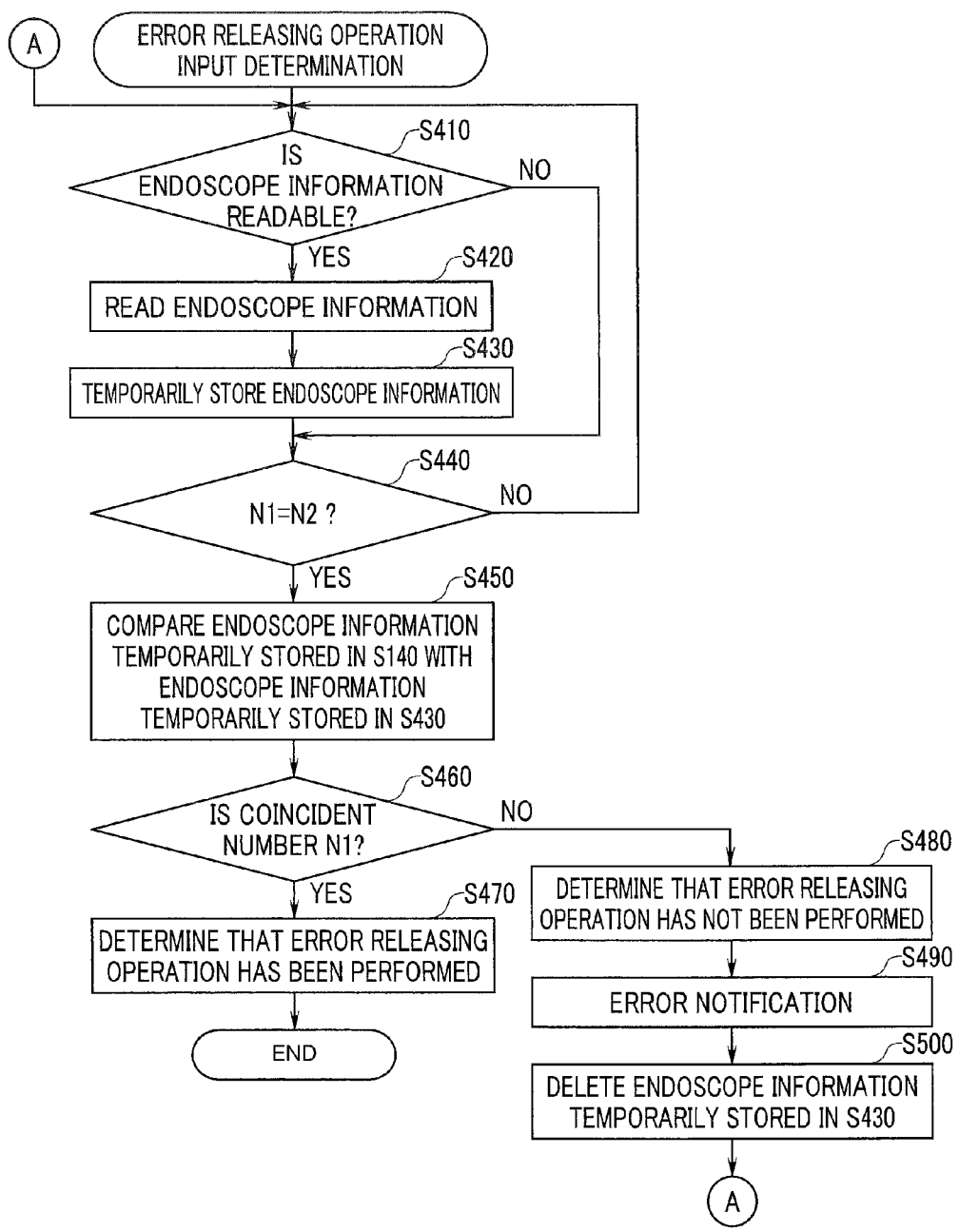
FIG. 10 is a flowchart of an error releasing operation input determination process of an endoscope reprocessor according to a fifth embodiment.

FIG. 10 is a flowchart of the error releasing operation input determination process of the endoscope reprocessor 1 according to the present embodiment. As described in the first embodiment, the control section 5 executes the error releasing operation input determination process illustrated in FIG. 10 after the notification section 8 starts the error notification. As described in the above-described first to third embodiments, the control section 5 causes the notification section 8 to start the error notification when the endoscope that has not been subjected to the endoscope information reading by the endoscope information reading section 9 is disposed inside the treatment tank 2, namely, when the first number N1 is different from the second number N2.

As illustrated in FIG. 10, in the error releasing operation input determination process according to the present embodiment, first, the control section 5 determines in step S410 whether the endoscope information reading section 9 can read the endoscope information. For example, the endoscope information reading section 9 can read the endoscope information when the RFID tag incorporated in or attached to the endoscope is brought into the range readable by the endoscope information reading section 9.

When the endoscope information reading section 9 cannot read the endoscope information in step S410, the process proceeds to step S440.

On the other hand, when the endoscope information reading section 9 can read the endoscope information, the process proceeds to step S420. In step S420, the control section 5 causes the endoscope information reading section 9 to read the endoscope information. Next, in step S430, the control section 5 temporarily stores the endoscope information read in step S420 in the memory section 5a.

In other words, execution of step S430 increases the number of pieces of the endoscope information temporarily stored in the memory section 5a by one piece, and increases the value of the first number N1. After step S430 is executed, the process proceeds to step S440.

In step S440, the control section 5 determines whether the first number N1 that is the number of endoscopes, the endoscope information of which has been read by the endoscope information reading section 9, is equal to the second number N2 that is the number of endoscopes disposed inside the treatment tank 2 detected by the number detection section 80 in step S170 of FIG. 3.

When the control section 5 determines in step S440 that the first number N1 is different from the second number N2, the process returns to step S410, and the processes in step S410 to step S430 mentioned above are repeated.

When the control section 5 determines in step S440 that the first number N1 is equal to the second number N2, the process proceeds to step S450.

In step S450, the control section 5 compares the endoscope information temporarily stored in the memory section 5a in step S140 of FIG. 3 with the endoscope information temporarily stored in the memory section 5a in step S430.

Then, in step S460, the control section 5 determines whether the number of pieces of endoscope information, the contents of which are coincident between the endoscope information temporarily stored in the memory section 5a in step S140 and the endoscope information temporarily stored in the memory section 5a in step S430 in the comparison in step S450, is equal to the first number N1.

For example, when the user performs the endoscope information reading motion by the endoscope information reading section 9 on all of the second number N2 of the endoscopes disposed inside the treatment tank 2 after the notification section 8 starts the error notification, the first number N1 becomes equal to the second number N2 (YES in step S440), and the number of pieces of endoscope information, the contents of which are coincident between the endoscope information temporarily stored in the memory section 5a in step S140 and the endoscope information temporarily stored in the memory section 5a in step S430, becomes equal to the first number N1 (YES in step S460).

Next, the process proceeds to step S470, and the control section 5 determines that the error releasing operation has been performed by the user. In other words, execution of step S470 results in determination of YES in step S220 of FIG. 3, and the process proceeds to step S230. In step S230, the control section 5 stops driving of the notification section 8, thereby stopping the error notification.

At this time point, the endoscope information temporarily stored in the memory section 5a is endoscope information obtained by executing the endoscope information reading again on all of the endoscopes that have been subjected to the reprocessing and are disposed in the treatment tank 2, during the execution of the error releasing operation input determination process. Also, some pieces of the endoscope information that have been subjected to the endoscope information reading again during the execution of the error releasing operation input determination process are coincident with the endoscope information that has been subjected to the endoscope information reading before the reprocessing is performed. This indicates that replacement of the endoscopes inside the treatment tank 2 are not performed after the reprocessing is performed until the execution of the error releasing operation input determination process. Thus, the endoscope reprocessor 1 according to the present embodiment makes it possible to accurately associate the endoscope information with the history information without omission.

After the execution of step S230, the process proceeds to step S190, and the control section 5 associates the endoscope information temporarily stored in the memory section 5a with the history information including information of the date on which the reprocessing is performed and the like, and stores the associated information as new management information in the memory section 5a. Then, in step S200, the control section 5 deletes the endoscope information temporarily stored.

In contrast, for example, when the user performs the endoscope information reading motion by the endoscope information reading section 9 on the endoscope that is not disposed inside the treatment tank 2 after the notification section 8 starts the error notification, this indicates that the endoscope information reading section 9 reads the endoscope information that should not be associated with the history information.

In this case, the number of pieces of endoscope information, the contents of which are coincident between the endoscope information temporarily stored in the memory section 5a in step S140 and the endoscope information temporarily stored in the memory section 5a in step S430, is different from the first number N1 (NO in step S460).

Next, the process proceeds to step S480, and the control section 5 determines that the error releasing operation by the user is not performed. In other words, execution of step S480 results in determination of NO in step S220 of FIG. 3.

Thereafter, the process proceeds to step S490, and the control section 5 drives the notification section 8 to notify, as an error, the fact that the endoscope that has been subjected to the endoscope information reading during the execution of the error releasing operation input determination process may be different from the endoscope that has been subjected to the reprocessing. Then, in step S500, the control section 500 deletes the endoscope information temporarily stored in the memory section 5*a* in step S430, and the process returns to step S410.

As mentioned above, the endoscope reprocessor 1 according to the present embodiment starts driving of the notification section 8 to start the error notification motion when the first number N1 that is the number of endoscopes, the endoscope information of which has been read by the endoscope information reading section 9, is different from the second number N2 that is the number of endoscopes disposed inside the treatment tank 2 detected by the number detection section 80. Then, in the present embodiment, the error notification is continued until endoscope information of all of the endoscopes disposed inside the treatment tank 2 is read by the endoscope information reading section 9, after the start of the error notification motion.

In this way, the endoscope reprocessor 1 according to the present embodiment prompts the user to perform the endoscope information reading on all of the endoscopes disposed inside the treatment tank 2 including the endoscope that has not been subjected to the endoscope information reading operation before the start of the reprocessing. Thus, according to the endoscope reprocessor 1 of the present embodiment, it is possible to prevent forgetting of the endoscope information reading by the endoscope information reading section 9, and to prevent mixing of the endoscope information of the endoscope that has not been subjected to the reprocessing. This makes it possible to accurately associate the endoscope information with the history information without omission.

The other components of the endoscope reprocessor 1 according to the present embodiment are similar to those of the first to third embodiments. Therefore, since the detection motion of the second number N2 by the number detection section 80 is executed simultaneously with the reprocessing also in the present embodiment, the waiting time period for execution of the detection motion of the second number N2 does not occur.

Sixth Embodiment

Next, a sixth embodiment of the present invention is described. In the following, only differences with the first to fifth embodiments are described, components similar to the components of the first to fifth embodiments are denoted by the same reference numerals, and description of the components is appropriately omitted.

Figure 11:
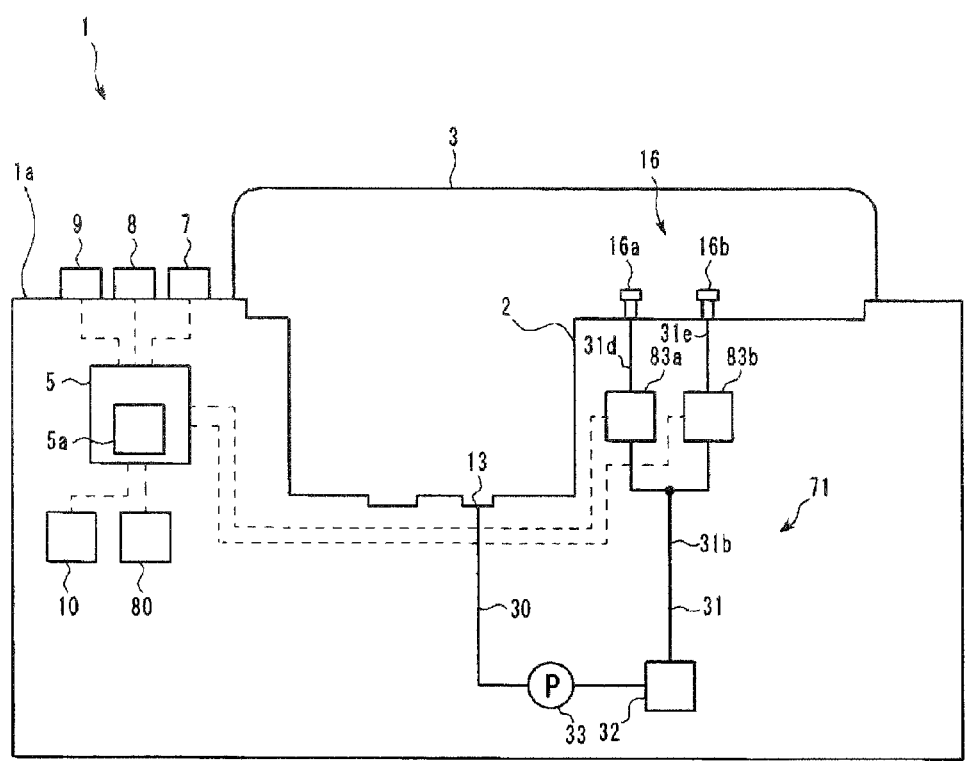
FIG. 11 is a diagram illustrating a configuration relating to a number detection section of an endoscope reprocessor according to a sixth embodiment.

The endoscope reprocessor 1 according to the present embodiment illustrated in FIG. 11 is different from the above-described first to fifth embodiments in the configuration to detect the second number N2 by the number detection section 80. FIG. 11 is a diagram illustrating a configuration relating to the number detection section 80 of the endoscope reprocessor 1 of the present embodiment.

The endoscope reprocessor 1 according to the present embodiment includes a first connector 16*a* and a second connector 16*b* in the treatment tank 2. The first connector 16*a* and the second connector 16*b* are included in the endoscope connection portion 16. In other words, the first connector 16*a* and the second connector 16*b* are connected with the pipe sleeve included in the endoscope through the cleaning tube.

The first connector 16*a* and the second connector 16*b* are connected with endoscopes that are different from each other and disposed inside the treatment tank 2, through the respective cleaning tubes. For example, when only one endoscope is disposed inside the treatment tank 2, one of the first connector 16*a* and the second connector 16*b* is connected with the endoscope through the cleaning tube.

Note that the first connector 16*a* and the second connector 16*b* may be directly connected with the respective endoscopes without the cleaning tube.

The first connector 16*a* and the second connector 16*b* are respectively connected with a first supply conduit 31*d* and a second supply conduit 31*e* of a liquid supply section 71 described later. The first connector 16*a* and the second connector 16*b* each include a valve. The valve is closed when the cleaning tube or the endoscope is not connected with the valve, and the valve is open when the cleaning tube or the endoscope is connected with the valve.

The liquid supply section 71 includes: the first supply conduit 31*d* and the second supply conduit 31*e* that are respectively connected with the first connector 16*a* and the second connector 16*b*; and a circulation pump 33 that supplies liquid to the first supply conduit 31*d* and the second supply conduit 31*e*.

The first supply conduit 31*d* and the second supply conduit 31*e* make the endoscope connection conduit 31*b* described in the first embodiment respectively communicate with the first connector 16*a* and the second connector 16*b*. When operation of the circulation pump 33 is started while liquid is reserved in the treatment tank 2, the liquid in the treatment tank 2 is supplied to the first supply conduit 31*d* and the second supply conduit 31*e* through the endoscope circulation conduit 30, the delivery conduit 31, and the endoscope connection conduit 31*b*.

The first supply conduit 31*d* and the second supply conduit 31*e* are respectively provided with a first flow sensor 83*a* and a second flow sensor 83*b* that detect whether fluid flows through the corresponding conduit. The first flow sensor 83*a* and the second flow sensor 83*b* are electrically connected with the control section 5, and provide information of measurement results to the control section 5.

The control section 5 acquires, based on the detection results of the first flow sensor 83*a* and the second flow sensor 83*b*, presence or absence of ejection of the liquid from the first connector 16*a* and the second connector 16*b* when the liquid supply section 71 supplies the liquid to the first connector 16*a* and the second connector 16*b*.

More specifically, when flow of the liquid in the first supply conduit 31*d* is detected by the first flow sensor 83*a* while the circulation pump 33 is driven, the control section 5 determines that the first connector 16*a* is open and the liquid is ejected from the first connector 16*a*. Likewise, when flow of the liquid in the second supply conduit 31*e* is detected by the second flow sensor 83*b* while the circulation pump 33 is driven, the control section 5 determines that the second connector 16*b* is open and the liquid is ejected from the second connector 16*b*. The control section 5 provides the determination results to the number detection section 80.

As mentioned above, the first connector 16*a* and the second connector 16*b* are open when the cleaning tube or the endoscope is connected. Thus, detection of the ejection of the liquid indicates that the cleaning tube or the endoscope is connected.

The number detection section 80 according to the present embodiment detects the second number N2 that is the number of endoscopes that are disposed inside the treatment tank 2 and are connected with the endoscope connection portion 16, based on the determination results of the open-close state of the first connector 16*a* and the second connector 16*b* by the control section 5 mentioned above.

For example, when one of the first connector 16*a* and the second connector 16*b* is open and the other is closed, the number detection section 80 detects that the second number N2 is one. Also, for example, when both the first connector 16a and the second connector 16b are open, the number detection section 80 detects that the second number N2 is two.

The other components of the endoscope reprocessor 1 according to the present embodiment are similar to the components of the above-described first to fifth embodiments. Therefore, also in the endoscope reprocessor 1 according to the present embodiment, the notification section 8 executes the error notification when the first number N1 is different from the second number N2, which makes it possible to prevent forgetting of the endoscope information reading by the endoscope information reading section 9.

Further, the number detection section 80 detects the second number N2 at the same time when the process of delivering the liquid to the conduit of the endoscope is executed in the reprocessing. Therefore, as with the first embodiment, since the detection motion of the second number N2 by the number detection section 80 is executed simultaneously with the reprocessing also in the present embodiment, the waiting time period for execution of the detection motion of the second number N2 does not occur.

Note that in the above-described present embodiment, the control section 5 determines the open-close state of each of the first connector 16a and the second connector 16b, based on the measurement results of the flowrates of the first supply conduit 31d and the second supply conduit 31e respectively by the first flow sensor 83a and the second flow sensor 83b. For example, even if the first flow sensor 83a and the second flow sensor 83 are replaced with pressure sensors that respectively measure pressure of the first supply conduit 31d and pressure of the second supply conduit 31e, the control section 5 can determine the open-close state of each of the first connector 16a and the second connector 16b.

Further, when each of the first connector 16a and the second connector 16b includes a sensor that detects the open-close state and outputs the detected state to the control section 5, the first flow sensor 83a and the second flow sensor 83b are unnecessary.

Figure 12:
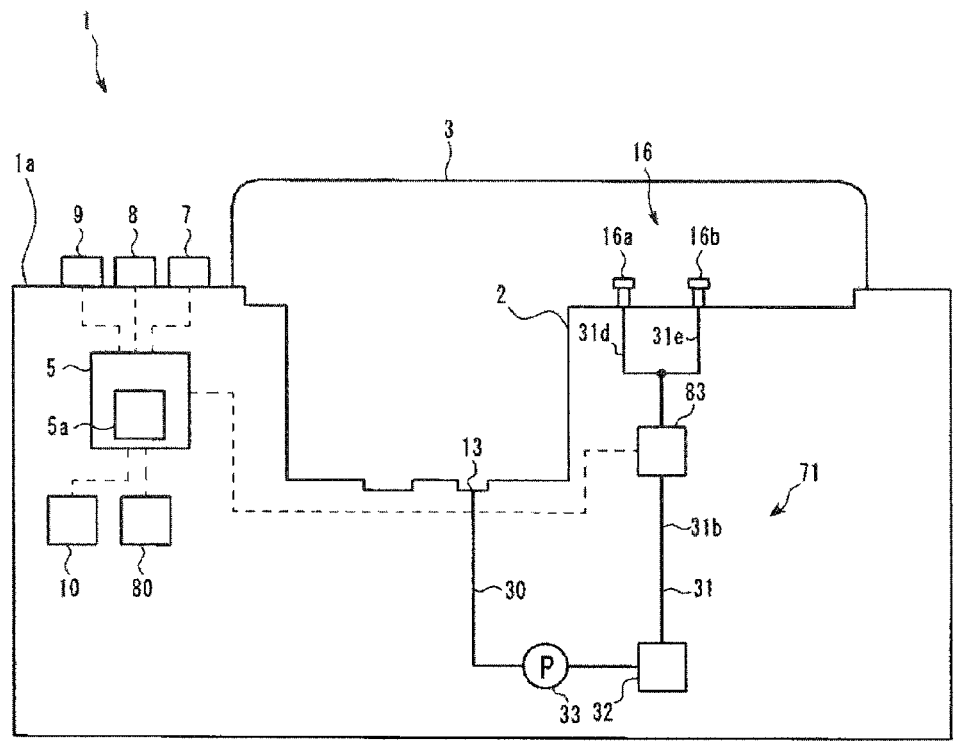
FIG. 12 is a diagram illustrating a configuration relating to a number detection section of an endoscope reprocessor according to a modification of the sixth embodiment.

FIG. 12 is a diagram illustrating a modification of the present embodiment. The modification illustrated in FIG. 12 is different from the above-described present embodiment in that a single flowrate sensor 83 is provided in the endoscope connection conduit 31b.

In the present modification, when the flowrate of the liquid in the endoscope connection conduit 31b detected by the flowrate sensor 83 exceeds a predetermined first threshold while the circulation pump 33 is driven, the control section 5 determines that both the first connector 16a and the second connector 16b are open. Also, when the flowrate of the liquid in the endoscope connection conduit 31b detected by the flowrate sensor 83 is equal to or lower than the above-described predetermined first threshold and exceeds a predetermined second threshold that is smaller than the predetermined first threshold while the circulation pump 33 is driven, the control section 5 determines that one of the first connector 16a and the second connector 16b is open and the other is closed.

When one of the first connector 16a and the second connector 16b is open and the other is closed, the number detection section 80 detects that the second number N2 is one. Also, when both the first connector 16a and the second connector 16b are open, the number detection section 80 detects that the second number N2 is two.

Note that, in the present modification, even if the flowrate sensor 83 is replaced with a pressure sensor that measures pressure inside the endoscope connection conduit 31b, the control section 5 can determine the number of open connectors out of the first connector 16a and the second connector 16b.

Seventh Embodiment

Next, a seventh embodiment of the present invention is described. In the following, only differences with the first to fifth embodiments are described, components similar to the components of the first to fifth embodiments are denoted by the same reference numerals, and description of the components is appropriately omitted.

Figure 13:
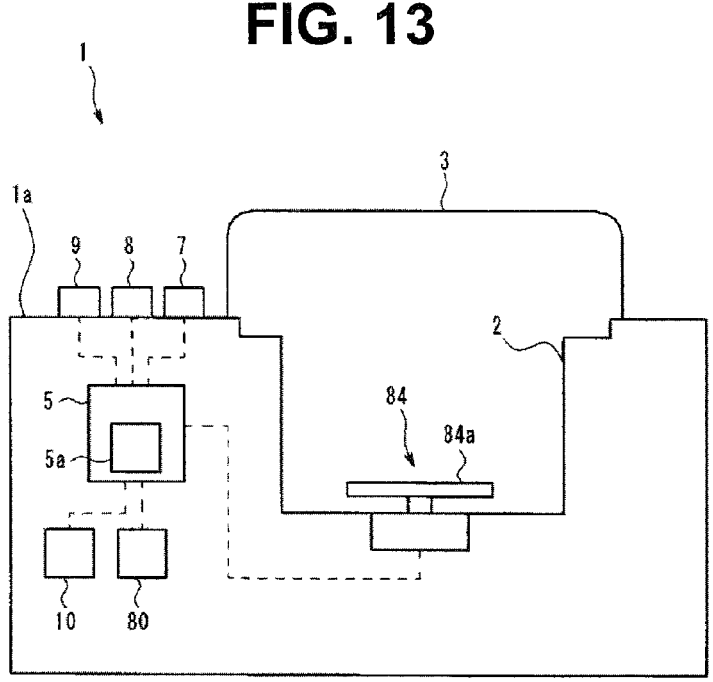
FIG. 13 is a diagram illustrating a configuration relating to a number detection section of an endoscope reprocessor according to a seventh embodiment.

The endoscope reprocessor 1 according to the present embodiment illustrated in FIG. 13 is different from the above-described first to fifth embodiments in configuration to detect the second number N2 by the number detection section 80. FIG. 13 is a diagram illustrating a configuration relating to the number detection section 80 of the endoscope reprocessor 1 according to the present embodiment.

The endoscope reprocessor 1 according to the present embodiment includes a mass measurement section 84 that measures a total mass Wa that is a total sum of masses of all of the endoscopes disposed inside the treatment tank 2. The mass measurement section 84 includes, for example, a mounting portion 84a disposed inside the treatment tank 2, and measures the mass of an object placed on the mounting portion 84a. For example, the mounting portion 84a has a shape holding a plurality of endoscopes inside the treatment tank 2. The mass measurement section 84 is electrically connected with the control section 5, and provides a measurement result of the total mass Wa to the control section 5. Note that the mass measurement section 84 may measure a mass including the treatment tank 2 itself.

The number detection section 80 calculates, from the value of the total mass Wa, the second number N2 that is the number of endoscopes disposed inside the treatment tank 2. For example, when the value of the total mass Wa exceeds a predetermined first threshold, the number detection section 80 detects that the second number N2 is two. Further, for example, when the value of the total mass Wa is equal to or lower than the predetermined first threshold and exceeds a predetermined second threshold that is lower than the first threshold, the number detection section 80 detects that the second number N2 is one.

The other components of the endoscope reprocessor 1 according to the present embodiment are similar to the components of the above-described first to fifth embodiments. Therefore, also in the endoscope reprocessor 1 according to the present embodiment, the notification section 8 executes the error notification when the first number N1 is different from the second number N2, which makes it possible to prevent forgetting of the endoscope information reading by the endoscope information reading section 9.

Eighth Embodiment

Next, an eighth embodiment of the present invention is described. In the following, only differences with the first to fifth embodiments are described, components similar to those of the first to fifth embodiments are denoted by the same reference numerals, and description of the components is appropriately omitted.

Figure 14:
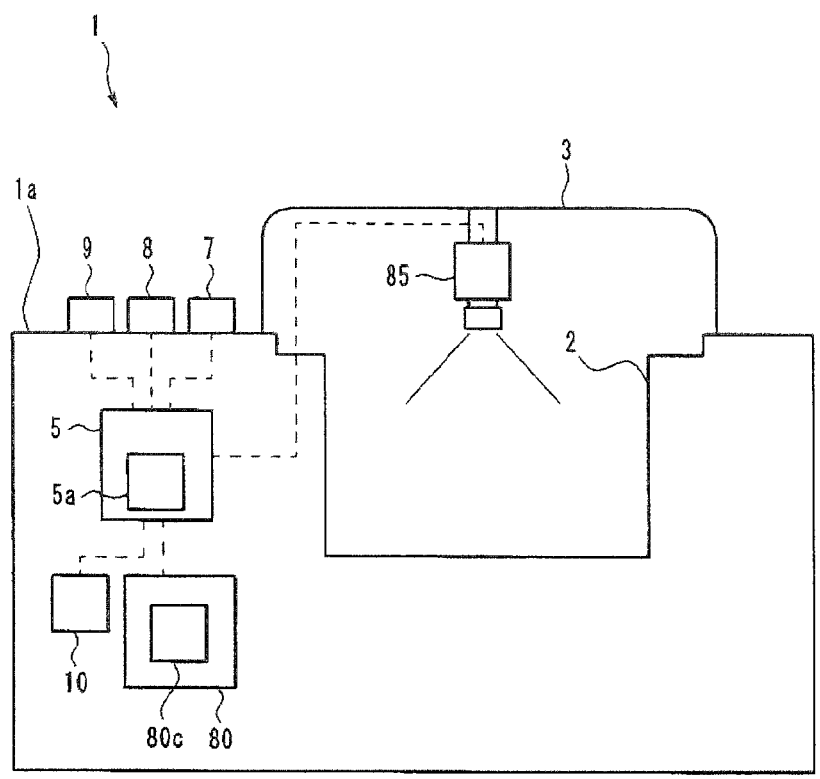
FIG. 14 is a diagram illustrating a configuration relating to a number detection section of an endoscope reprocessor according to an eighth embodiment.

The endoscope reprocessor 1 according to the present embodiment illustrated in FIG. 14 is different from the above-described first to fifth embodiment in configuration to detect the second number N2 by the number detection section 80. FIG. 14 is a diagram illustrating a configuration relating to the number detection section 80 of the endoscope reprocessor 1 according to the present embodiment.

The endoscope reprocessor 1 according to the present embodiment includes a camera 85 that picks up an image of all of endoscopes disposed inside the treatment tank 2 within a field of view of the camera 85. The camera 85 is electrically connected with the control section 5, and provides the picked-up image to the control section 5.

The number detection section 80 includes an image processing section 80c that calculates, from the image picked up by the camera 85, the second number N2 that is the number of endoscopes disposed inside the treatment tank 2. For example, the image processing section 80c detects, from the image, a part having a characteristic shape such as an operation handle included in the endoscope, through image processing such as pattern matching. The number detection section 80 calculates the second number N2 from the number of parts detected by the image processing section 80c. Note that the number detection section 80 may calculate the number of endoscopes in the image from the percentage of the area of the endoscopes in the image, and use the number of the endoscopes as the second number N2.

The other components of the endoscope reprocessor 1 according to the present embodiment are similar to the components of the above-described first to fifth embodiments. Therefore, also in the endoscope reprocessor 1 according to the present embodiment, the notification section 8 executes the error notification when the first number N1 is different from the second number N2, which makes it possible to prevent forgetting of the endoscope information reading by the endoscope information reading section 9.

Note that the present invention is not limited to the above-described embodiments, and may be appropriately modified without departing from the scope and spirit of the invention as set forth in the appended claims and the entire specification, and the endoscope reprocessor accompanying such modification is also incorporated in the technical scope of the present invention.

What is claimed is:

1. An endoscope reprocessor comprising:
   an endoscope information reading section configured to read endoscope information from a plurality of endoscopes;
   a treatment tank in which the plurality of endoscopes are disposed;
   a liquid supply section configured to supply liquid to the treatment tank;
   a first connector disposed in the treatment tank, and including a first valve configured to be put into an open state from a closed state through connection with an endoscope or a cleaning tube;
   a second connector disposed in the treatment tank, and including a second valve configured to be put into the open state from the closed state through connection with an endoscope or a cleaning tube;
   a liquid supply conduit connecting the first connector and the second connector with the liquid supply section;
   a flowrate sensor disposed in the liquid supply conduit;
   a number detection section configured to detect a number of the endoscopes disposed in the treatment tank, the number detection section being connected with the flowrate sensor, the number detection section detecting, based on a measurement value of the flowrate sensor, a number of connectors whose valve is in an open state from the first and second connectors, and converting a result of the detecting into the number of endoscopes disposed in the treatment tank;
   a notification section configured to execute error notification; and
   a control section connected with the notification section and configured to:
      take a quantity of endoscopes read by the endoscope information reading section as a first number and the number of endoscopes disposed in the treatment tank as detected by the number detection section as a second number, and determine whether the first number is equal to the second number; and
      drive the notification section to execute error notification when the control section determines that the first number is different from the second number.

* * * * *